(12) United States Patent
Trapani

(10) Patent No.: US 10,010,633 B2
(45) Date of Patent: Jul. 3, 2018

(54) ROOM STERILIZATION METHOD AND SYSTEM

(71) Applicant: Steriliz, LLC, Rochester, NY (US)

(72) Inventor: Sam Trapani, Rochester, NY (US)

(73) Assignee: Steriliz, LLC, Rochester, NY (US)

( * ) Notice: Subject to any disclaimer, the term of this patent is extended or adjusted under 35 U.S.C. 154(b) by 336 days.

(21) Appl. No.: 14/263,774

(22) Filed: Apr. 28, 2014

(65) Prior Publication Data

US 2015/0086420 A1 Mar. 26, 2015

Related U.S. Application Data

(63) Continuation-in-part of application No. 13/964,874, filed on Aug. 12, 2013, now Pat. No. 9,345,798.

(Continued)

(51) Int. Cl.
*A61L 2/10* (2006.01)
*A61L 2/24* (2006.01)
*A61L 2/20* (2006.01)
*A61L 9/015* (2006.01)
*A61L 9/20* (2006.01)

(Continued)

(52) U.S. Cl.
CPC ............ *A61L 2/10* (2013.01); *A61L 2/202* (2013.01); *A61L 2/208* (2013.01); *A61L 2/24* (2013.01); *A61L 9/015* (2013.01); *A61L 9/20* (2013.01); *A61L 2202/11* (2013.01); *A61L 2202/14* (2013.01); *A61L 2202/16* (2013.01); *A61L 2202/25* (2013.01); *G01J 1/429* (2013.01); *G01J 2001/0276* (2013.01)

(58) Field of Classification Search
CPC ......................................................... A61L 2/10
See application file for complete search history.

(56) References Cited

U.S. PATENT DOCUMENTS 3,861,875 A 2/1975 Larry
5,114,670 A 5/1992 Duffey
(Continued)

OTHER PUBLICATIONS

Mao et al. Sampling Frequency Optimization in Wireless Sensor Network-Based Control System. Shanghai Jiao Tong Unitversity. APWeb Workshops. 2006.*

(Continued)

*Primary Examiner* — Donald R Spamer
(74) *Attorney, Agent, or Firm* — Hulsey, P.C.

(57) ABSTRACT

A sterilization system consisting of a mobile emitter, a sensing subsystem and a data logging subsystem is described. The emitter has one or more UV emitting lamps or devices. The sensing system comprises at least one remote UV sensor and at least one door sensor. The door sensor comprises a safety shut off door detector and may contain an emergency stop detector and arming detector to protect people from being exposed to UV energy. The system has a remote control for starting, stopping and setting system parameters which include but are not limited to: treatment time, dosage, room size, room number, unit number, floor, facility name, operator name, operator identification number, password, default dosage values, dosage, and patient identification number. The number of treatments per unit of time can be maximized because of the use of incident light measurement.

20 Claims, 28 Drawing Sheets

Related U.S. Application Data which is a continuation-in-part of application No. 13/446,563, filed on Apr. 13, 2012, now abandoned.

(60) Provisional application No. 61/475,722, filed on Apr. 15, 2011.

(51) Int. Cl.
*G01J 1/42* (2006.01)
*G01J 1/02* (2006.01)

(56) References Cited

U.S. PATENT DOCUMENTS

| | | | |
|---|---|---|---|
| 5,650,800 | A | 7/1997 | Andrew |
| 6,592,816 | B1 | 7/2003 | Ebel et al. |
| 6,656,424 | B1 | 12/2003 | Deal |
| 6,662,099 | B2 | 12/2003 | Ara, et al. |
| 6,911,177 | B2 | 6/2005 | Deal |
| 7,638,970 | B1 * | 12/2009 | Gebhard .............. F21L 4/08 320/107 |
| 8,067,750 | B2 | 11/2011 | Deal |
| 2005/0168154 | A1 | 8/2005 | James et al. |
| 2005/0242290 | A1 | 11/2005 | Joe et al. |
| 2006/0120915 | A1 | 6/2006 | Lewandowski |
| 2007/0008117 | A1 | 1/2007 | Parker et al. |
| 2007/0023710 | A1 | 2/2007 | Tom |
| 2007/0048176 | A1 * | 3/2007 | Orrico ................ A61L 2/14 422/29 |
| 2007/0050191 | A1 | 3/2007 | Chris et al. |
| 2007/0099643 | A1 | 5/2007 | James et al. |
| 2007/0102025 | A1 | 5/2007 | Ahn et al. |
| 2010/0061887 | A1 * | 3/2010 | Harper ................. A61L 2/10 422/24 |
| 2011/0168898 | A1 | 7/2011 | Statham et al. |

OTHER PUBLICATIONS

"Enhanced Environmental Disinfection Systems", Enhanced Environmental Disinfection Systems, Health Devices, May 2011. pp. 150-162, ECRI Institute, www.ecri.org., May 2011, 150-162.

"UV Power Meter", Hamamatsu. "UV Power Meter". taken from screen capture by the Internet Archive Wayback Machine on Jan. 2, 2010.

Boyce, John M. et al., "Terminal Decontamination of Patient Rooms Using an Automated Mobile UV Light Unit", Boyce, John M. et al., Terminal Decontamination of Patient Rooms Using an Automated Mobile UV Light Unit, Infection Control and Hospital Epidemiology, Aug. 2011. pp. 737-742, vol. 32, No. 8, The Society for Healthcare Epidemiology of America, USA., Aug. 2011, 737-742.

Rutala, William A. et al., "Are Room Decontamination Units Needed to Prevent Transmission of Environmental Pathogens?", Rutala, William A. et al., Are Room Decontamination Units Needed to Prevent Transmission of Environmental Pathogens?, Infection Control and Hospital Epidemiology, Aug. 2011. pp. 743-747, vol. 32, No. 8, The Society for Healthcare Epidemiology of America., Aug. 2011, 737-742.

\* cited by examiner

FIGURE 26B
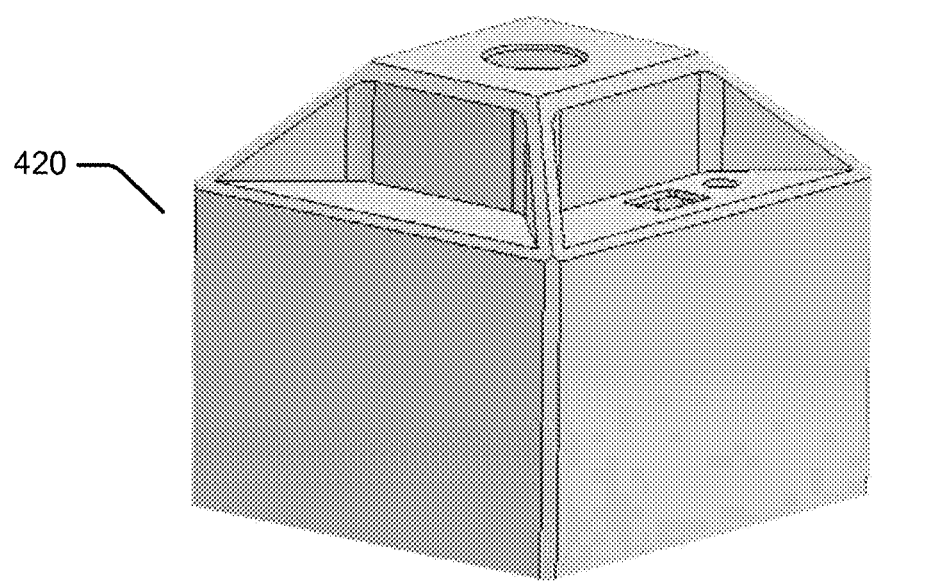
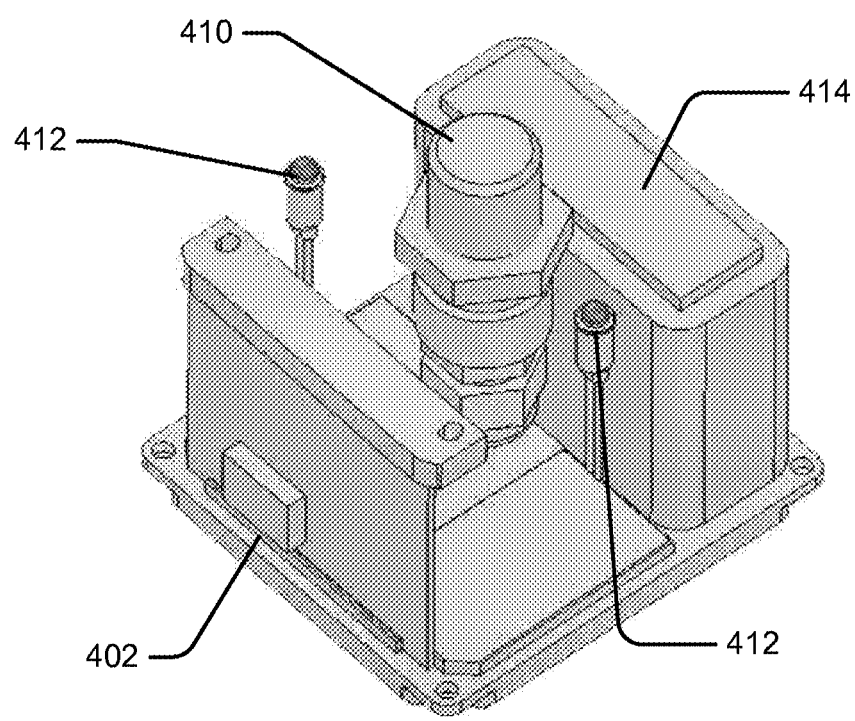
FIGURE 26A

ROOM STERILIZATION METHOD AND SYSTEM

CROSS-REFERENCE TO RELATED APPLICATIONS

This application claims priority to U.S. Utility patent application Ser. No. 13/964,874 filed Aug. 12, 2013, which claims priority to U.S. Utility patent application Ser. No. 13/446,563 filed Apr. 13, 2012, which claims priority to U.S. Provisional Patent Application Ser. No. 61/475,722 filed Apr. 15, 2011.

Furthermore, this application claims priority to U.S. Provisional Patent Application Ser. No. 61/816,530 filed Apr. 26, 2013.

Furthermore, this application claims priority to U.S. Provisional Patent Application Ser. No. 61/887,398 filed in October 2013.

All aforementioned application are hereby incorporated by reference in its entirety.

FIELD OF THE INVENTION

The present disclosure relates to disinfection. More specifically, the present disclosure relates to disinfection of pathogens using ultraviolet (UV) light.

BACKGROUND OF THE INVENTION

In the U.S. each year, more people die from hospital infections than from AIDS, breast cancer, and auto accidents combined. These infections are the fourth leading cause of death, with current annual estimates of 2,000,000 infections, 100,000 deaths, and added costs of $45 billion. Somewhere between 5-10% of all patients admitted to a hospital acquire an infection while in that hospital. Even with such extreme statistics, many industry experts consider the problem to be severely underestimated.

Currently, *Clostridium difficile* (*C. diff*) is one of the most problematic pathogens in the healthcare industry. It causes *C. diff* Infection (CDI) that sickens and kills humans. The Centers for Disease Control (CDC) states that *C. diff* spores are transferred to patients mainly via the hands of healthcare personnel who have touched a contaminated surface or item. They also say that to reduce the chance of spreading pathogens and subsequent disease, surfaces must be cleaned more effectively.

Current cleaning methods, such as chemical disinfection, are not working as stand-alone practices, and additional measures need to be taken to reduce the risk to patient and healthcare professionals'. For more than 75 years UV light has been used to destroy pathogens in water supplies and heating, ventilation, and air-conditioning (HVAC) systems. In recent years, products have been developed that utilize UV to disinfect surfaces and air.

In 1892, Professor Marshall Ward demonstrated that it was primarily the UV portion of the spectrum of light that had the ability to inactivate the DNA of pathogens thereby making them unable to multiply. Medical uses of UV light include sterilization of surfaces and air without the use of chemicals. There are many well documented studies that identify the specific amount (dosage) of UV light necessary to disinfect and sterilize surfaces and air.

One type of existing UV disinfection equipment uses either a manually operated switch or a timer to deliver UV light for a period of time. Another type of existing UV disinfection equipment is a system that measures reflected UV light, generally at the emitter, to control how much time the UV light is delivered. Both of these types of equipment are unable to definitively deliver a specific dosage to a surface or volume of air because there is no measurement being taken at the location of interest. This problem results in surfaces and air being exposed to too much, or too little, UV radiation. In the case of over-treating, excess treatment time, which slows down the facility's operations thus adding to operating costs and reducing throughput, and excess exposure of room surfaces to UV radiation, which causes faster breakdown of the materials the surfaces are made from, may occur. In the case of under-treating, disinfection or sterilization is not assured, which may result in reduced efficacy of disinfection procedure and increased exposure to liability.

BRIEF SUMMARY OF THE INVENTION

Therefore, it is an object of this disclosure to provide room disinfection and/or sterilization methods and apparatuses that satisfy the demands discussed above while improving on known shortcomings in the art.

The present disclosure discusses a mobile system which, automatically delivers UV-C light to all surfaces within a treatment space, including hard-to-clean, high-touch surfaces such as keyboards, computers, and bed rails, yielding a significantly more sterile, safer environment.

When compared to other systems and techniques, this disclosure provides faster processing-time and critical data capture that clearly demonstrates treated areas have received the necessary dosage of UV-C light needed to eradicate dangerous pathogens effectively. Another benefit of UV-C disinfection is that it leaves no harmful residue or vapors. After sterilization, the room is immediately available for occupancy.

The present disclosure comprises a room disinfection and sterilization system utilizing UV light to cause permanent and fatal injury to the pathogens that cause illness and death to humans. This system includes an emitter that produces UV light, one or more remote wired or wireless UV light sensors that measure the intensity of UV light incident upon them, one or more remote (wired or wireless) door sensor safety stop switches which cause the system to stop emitting UV light in the event that the door being monitored is opened or if the safety stop switches is depressed, a (wired or wireless) remote control to operate the system, and a central computer with wireless local area network (WLAN, e.g. Wi-Fi, WICAD, bluetooth, 802.11, 802.15, 3G, 4G, CDMA, or other suitable technology) connect-ability to access the internet and provide local and remote logging of disinfection cycles or jobs. In some embodiments, the device of the present disclosure may include its own Wi-Fi access point, along with an Internet bridge (for example, a cellular modem). In some embodiments, the remote control may be a standard iPod or other PDA/smartphone/tablet/handheld device.

The present disclosure delivers lethal UV-C light doses into all areas of complex environments, destroying viruses, spores, and drug-resistant bacteria, even in a room's shadowed areas. Its remote sensors make this the only system that can measure how much UVC energy reaches every corner of a treatment space.

The present disclosure employs at least one remote sensor which definitively measures the precise dosage of UV light delivered to the location of interest. Data recording and reporting are necessary for tracking and analyzing infections acquired in facilities where disinfection occurs. A significant difference between the present disclosure and existing equipment and systems is the ability to store, retrieve, report and analyze such data. The present disclosure employs local storage of such data on the memory of its computer controller and remote data storage via up-linking to a remote internet host server for others to access.

The present disclosure delivers a system capable of managing the sterility of a facility through managing a plurality of UV-C sterilization devices. Furthermore, the present disclosure provides a system, method and apparatus for implementing sterilization, tracking sterilization, as well as measuring both the status of sterilization procedures but also the associated effectiveness across a plurality of factors, parameters, periods and locations.

The present disclosure describes a room disinfection and sterilization system wherein the sensors, when not in use, are able to be attached to the system for transportation and charging.

The present disclosure details a UV sensor capable of detecting motion within proximity to the sensor, and upon detection, communicating to the central processing unit. The central processing unit can stop or pause emission of UV radiation in response to stimuli detected by sensors, including but not limited to: the detection of motion in the environment being sterilized, and by the changing in state (i.e. open or closing) of a door associated within the environment.

The present disclosure details a UV emitting device capable of moving within an environment in response to stimuli from sensors to ensure the completeness and effectiveness of a sterilization procedure.

A present disclosure also describes a system combining both door and motion sensors to protect people and animals from being exposed to UV energy.

These and other advantages of the disclosed subject matter, as well as additional novel features, will be apparent from the description provided herein. The intent of this summary is not to be a comprehensive description of the subject matter, but rather to provide a short overview of some of the subject matter's functionality. Other systems, methods, features and advantages here provided will become apparent to one with ordinary skill in the art upon examination of the following FIGURES and detailed description. It is intended that all such additional systems, methods, features and advantages included within this description, be within the scope of the claims.

BRIEF DESCRIPTION OF THE FIGURES

The features, nature, and advantages of the disclosed subject matter may become more apparent from the detailed description set forth below when taken in conjunction with the FIGURES in which like reference numerals indicate like features and wherein:

Figure 15:
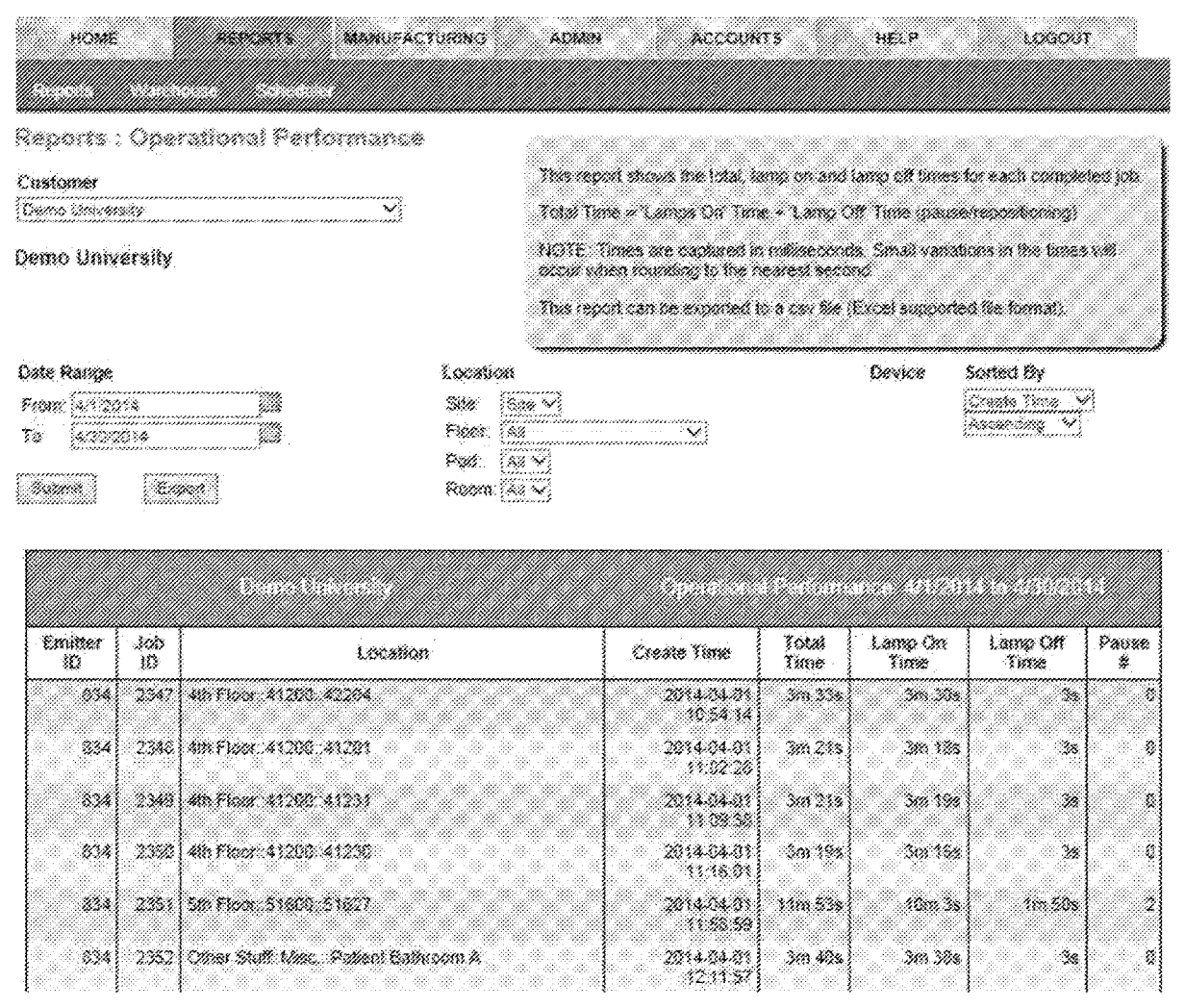

FIG. 15 presents an exemplary operational performance report as described in the present disclosure.

FIG. 16 presents an exemplary room clean sweep analysis report as described in the present disclosure.

FIG. 17 presents an exemplary room disinfection job summary report as described in the present disclosure.

FIG. 18 presents an exemplary room disinfection treatment summary report as described in the present disclosure.

FIG. 19 presents an exemplary room frequency report as described in the present disclosure.

FIG. 20 presents an exemplary room last treated report as described in the present disclosure.

FIG. 21 presents an exemplary room treatment overview report as described in the present disclosure.

FIG. 22 presents an exemplary room treatment statistics report as described in the present disclosure.

FIG. 23 presents an exemplary team performance report as described in the present disclosure.

FIG. 26A presents an internal configuration of an exemplary sensor.

FIG. 26B presents a configuration for a sensor enclosure.

DETAILED DESCRIPTION OF ILLUSTRATIVE EMBODIMENTS

The present disclosure may be understood more readily by reference to the following detailed description, examples, FIGURES, and claims, and their previous and following description. However, before the present devices, systems, and/or methods are disclosed and described, it is to be understood that this disclosure is not limited to the specific devices, systems, and/or methods disclosed unless otherwise specified, as such, can vary. It is also to be understood that the terminology used herein is for the purpose of describing particular aspects only and is not intended to be limiting.

As used in the specification and the appended claims, the singular forms "a," "an" and "the" may include a plurality of referents. Thus, for example, reference to "a sensor" can include two or more such sensors.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Reference will now be made in detail to certain embodiments of the disclosure, examples of which are illustrated in the accompanying FIGURES. Wherever possible, the same reference numbers are used throughout the FIGURES to refer to the same or like parts.

Figure 1A:
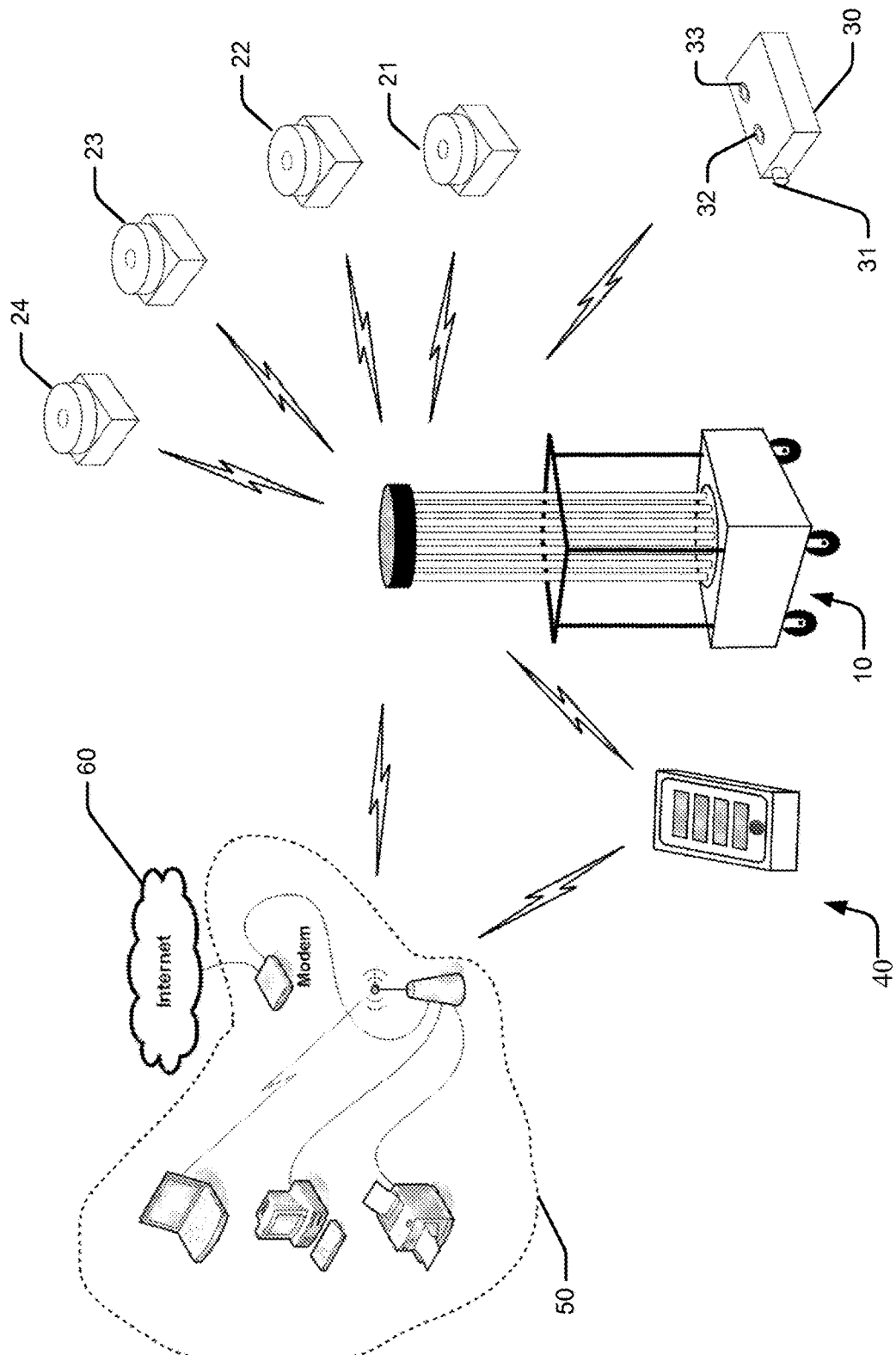
FIG. 1A is a perspective view of a disinfection system of the present disclosure.

FIG. 1A illustrates a sterilization system comprising an emitter 10, a sensing system consisting of UV sensors 21-24, door sensor 30, remote control 40, optional wireless local area network (WLAN) 50, and optional Internet connection 60 for the optional WLAN.

In more detail, still referring to FIG. 1A as well as FIG. 1B, we begin with a discussion of the emitter subsystem. This subsystem consists of an emitter 10 which is a mobile structure on wheels with a plurality of lamps that emit UV light when energized by their corresponding electronic ballast(s). Other forms of an emitter may be a mobile structure with another means for transporting without the use of integrated wheels, or a stationary structure. Neither of these, or other forms of transportation, are precluded. Also contained in this subsystem is central computer 11, which executes a software program that controls energization of the lamps and ballasts through the cycling of an interconnected relay. Computer 11 communicates with the sensing subsystem's remote UV sensors 21-24, which provide UV light level readings used by computer 11 to determine when a previously programmed dose of incident UV light has been delivered to each of the remote sensor locations.

The dosage setting is determined by the specific pathogen(s) the operator wants to eradicate. For example, to deliver a disinfection dosage of UV light for the elimination of *Escherichia coli* (*E. coli*) requires approximately 6,600 microwatt-seconds/centimeter-squared for a 100:1 reduction (2 log) in *E. coli*; thus the setting would be 6,600, or a representative setting thereof. Existing systems and equipment do not utilize remote sensor(s) for surface and air disinfection therefore they do not offer a way to definitively deliver this dosage to a remote location. The appropriate dosages to provide a particular log reduction in a particular pathogen are well known in the art, and this disclosure is not limited to any particular pathogen, disinfection level, or UV dosage.

Because UV light is harmful to humans, computer 11 communicates with door sensor 30, and if the door being monitored by the door sensor 30 is opened during a disinfection cycle, which may indicate a person is entering or has entered the room being treated, the lamps may be immediately turned off to prevent injury. The system may include a human-computer interface, hereafter HCI, which may be accomplished via remote control 40, and can be used to configure the type and number of sensors to be used for a particular job; to select the minimum dosage of UV light to deliver to each UV sensor; to begin, pause and end a job; and to view job reports stored on computer 11. Pausing the job may be advantageous for various reasons, including the possibility of re-positioning the emitter mid-job in order to obtain more complete sterilization of the room. Computer 11 communicates with a remote web server, via the optional internet connected WLAN 50 (if present), to post job reports and statuses for remote access by password-protected users. The emitter subsystem may contain a battery for keeping the computer energized when the subsystem isn't plugged into the facility's electric utility. This battery may be automatically recharged as needed from the facility's electric utility when the subsystem is plugged in. The emitter subsystem also has docks for recharging system sensors that operate by battery power.

Optional components of the present disclosure may be included in order to increase efficacy against particular pathogens. For example, in addition to using UV light, the device may further use a humidity generating device, an ozone generating device, and/or a vaporized hydrogen peroxide gas generating device. The combination of these optional components may provide for more effective and efficient disinfection than UV alone.

An integral part of the sterilization system is the sensing subsystem of FIG. 1A. The UV light sensing system will measure actual incident light at least one particular site(s) in an area. An advantage of using incident light over reflected light is that with incident light, sensors may be placed at any site to guarantee that UV radiation reaches a certain minimum dosage at that site. UV sensors 21-24 are designed to measure the total UV light incident upon them. Once all active sensors have received the desired dose, the disinfection procedure is considered complete. One method of measuring total incident UV light is to employ a cosine-corrected sensor, which accounts for all light incident upon it from a full 180 degree angle. Another method utilizes multiple sensors, incorporated into a single sensor array, to measure the UV light from various angles of incidence and then uses an algorithm to integrate the total light incident upon the sensors to obtain the total incident light from a full 180 degree angle. There are other known methods of measuring the total incident UV light upon a sensor, which are not precluded. For example, the sensors may make one or more instantaneous light measurements (perhaps after waiting for an initial warm-up period), and then calculate total dosage by assuming that the light level remains constant. Unless all the energy is integrated accurately, regardless of the method, it is difficult to determine the actual dosage of UV light delivered. Further, by measuring incident light, the system will not over-radiate an area. This allows for the shortest time for disinfection treatment before re-deployment into another area.

Over-radiating an environment is disadvantageous because UV radiation may cause unnecessary damage to surfaces in the area. This is in addition to the fact that fewer areas may be finished per unit time. When operating, the UV sensor(s) are designed and programmed to continually measure incident UV light. The intensity measured may be converted into a voltage, which is sampled by an analog to digital (A/D) converter, which is part of the UV sensor sub-system. The digital data may then be communicated to central computer 11. In addition to the intensity, a remote sensor may communicate a value representing the charge state of its internal battery. In this way, central computer 11 can be informed ahead of time how much battery life may be left in each remote sensor. One embodiment of this communication is wireless, but wired operation is not precluded. Wireless operation can be accomplished from any number of remote UV sensors back to central computer 11 using one of any number of wireless protocols. An example implementation uses four UV sensors 21-24, but the system may support any number of UV sensors. An example wireless protocol is the 802.15.4 Zigbee standard. In addition to wireless UV sensors 21-24, wireless door sensor 30 is included in the network of FIG. 1A. Wireless UV sensors 21-24 may be rechargeable battery operated units. Nonrechargeable or AC-powered units are not precluded. While in operation, the unit may operate completely on battery power. When not in operation, the sensor can be stored in its cradle on the emitter unit, or some other location, at which time re-charging occur. The set of sensors are operated such that they transmit with different time periods allowing for a lower probability that multiple units will transmit at the same time. A further embodiment uses buffering of the data at central computer 11 so that if multiple transmissions by sensors occur, the receiver at central computer will not miss any one of them. Another embodiment is for central computer 11 to initiate the request for data from the door and UV sensors on a one-by-one basis thereby eliminating the potential for two units to transmit at the same time. The UV sensors 21-24 are expected to see a relatively constant incident light intensity, and as such, time between transmissions, or the transmission period, can be relatively long. An example transmission period is 10 seconds, but this could range from as short as a few milliseconds to as long as several hours and is easily changed by the operator via the system software.

For example, in the case of a 10 second transmission period, the individual sensors can, in one embodiment, be programmed to retransmit at a time period equal to a prime number of milliseconds close to 10 seconds or 10,000 milliseconds. For example, sensor 1 might transmit at 9949 milliseconds, sensor 2 at 9967 milliseconds, sensor 3 at 9973 milliseconds and sensor 4 at 10007 milliseconds. These are all prime numbers of milliseconds close to 10 seconds. Setting the transmission period to these time periods greatly reduces the probability of two or more transmissions occurring at the same time. This does not preclude the use of similar time periods amongst UV sensors 21-24 as well.

Central computer 11 may receive the UV sensors' transmissions at the programmed transmission times and then calculate the time difference between receptions of information from each individual sensor in order to integrate the total incident light energy from each sensor and ensure that at least the prescribed dosage has been delivered to each particular sensor location.

This scheme provides another safeguard, because central computer 11 can detect if no messages are being received from a particular sensor for some predetermined period of time from the time the last transmission was received. This condition could occur because of a completely discharged battery or a defect in the sensing unit, in which case operator interaction may be required.

Each system may be equipped with door sensor 30 (or in some embodiments multiple door sensors) for emergency shutoff purposes. Door sensor 30 includes door detector 31 such that if the associated door opens or closes, central computer 11 will get a notification. If this event occurs while emitter 10 is operating and emitting UV light, then central computer 11 may shut down emitter 10. In addition to door detector 31, door sensor 30 also includes emergency shutoff detector 32, which could be used by an operator to shut down the system even if the door is closed. All of these events are distinguishable by central computer 11 by the message sent to it from door sensor 30. That is, central computer 11 will be able to know which of the above mentioned events occurred because of the digital information transmitted to it.

Latching may be provided on emergency shutoff detector 32. Thus, once emergency shutoff detector 32 is actuated, the indication will remain until reset. The current reset condition occurs when the door is open; however, other methods to reset are possible. Door sensor 30 may also communicate its battery state back to central computer 11 so that the system will know when the battery may need to be re-charged and may notify an operator in such an event.

Once the remote sensor(s) and UV emitter are placed where desired, the operator exits the room and begins the activation sequence by placing door sensor 30 in position at the door such that the sensor can detect if the door is opened or closed, or if there is a change from open to closed or vice-versa.

Next, the operator must actuate arming detector 33 located on the door sensor 30. A designed safety feature may prevent the system from being armed unless door sensor 30 indicates the door is closed. An open door or a door that is closed when armed and then opened may reset the system to the unarmed state. This design requires the operator to make sure that the door is closed before re-arming emitter 10.

This is of course only one embodiment of a method to arm the system. Another wired or wireless arming detector placed directly on the emitter could also provide for a similar function. Under this condition, the door must be open to arm the system. If the door is open, the operator could actuate the arming detector on the emitter. After this detector is actuated and latched (programmed to keep its state as "armed"), the door must close. Once the door is closed, remote control 40 could start the system. If the door has not closed, remote control 40 will not be able to start emitter 10. If the door opened after the emitter started, the emitter would shut down and cease emitting UV light.

Emitter 10 may include one or more additional "drone" emitters. These drone emitters are additional lights that may be added to the space in order to increase coverage and/or brightness of the UV radiation thereby decreasing sterilization time. The drone emitter(s) may be controlled by central computer 11 either by wired or wireless communications.

Door sensor 30 may encode the different switch conditions into a unique voltage measurement. This voltage may be converted to a digital value by an A/D converter, which may be part of door sensor 30 and then sent to central computer 11. The existence of the 3 detectors creates a maximum of 8 different voltage settings. In one embodiment with arming detector 33 as part of door sensor 30, when the door is open, the state of the arming detector is in a "don't care" condition (X). As such, only 6 states need be detected. An example embodiment is shown in Table 1 below, but this does not preclude the use of other techniques to distinguish between the multiple states of door sensor 30.

TABLE 1

An example encoding of the door switch

| Door Position | Arming Switch | Emergency Shutoff Switch | Operation | Voltage (V) | A/D (hex code) |
|---|---|---|---|---|---|
| Closed | Armed | Open | Normal | 1 | AAA |
| Closed | Unarmed | Open | Waiting for Arm | .82 | 8BF |
| Closed | Armed | Closed | Shutdown | 1.39 | ED3 |
| Closed | Unarmed | Closed | Shutdown | 1.21 | CE8 |
| Open | X | Open | Shutdown | 0 | 000 |
| Open | X | Closed | Shutdown | .39 | 428 |

Because door sensor 30 may communicate critical information, its time period between transmissions may advantageously be shorter than that of UV sensors 21-24 so that the system can react more quickly to an emergency shutoff event. As such, time periods on the order of 1, typically 0.5 to 1.5, seconds are recommended, but not required. Similarly to UV sensors 21-24, the transmission time for the door sensor 30 could be selected to be a prime number around 1 second to avoid periodic radio frequency (RF) transmissions with the UV sensor group as previously discussed.

Central computer 11 may also be timing the receipt of the messages from door sensor 30. Should central computer 11 not receive a message from door sensor 30 within some maximum time duration, it may shut down the system so that the operator can determine the cause of the loss of door sensor 30 messages. A system malfunction or a discharged battery may be probable causes.

Another system related issue has to do with the identification of UV sensors as opposed to door sensors. Each sensor may have a unique identification number assigned to it. A rule may be used to easily identify the distinction between a UV sensor and a door sensor. An example embodiment would be to use even identification numbers for the door sensors and odd identification numbers for the UV sensors. However, other coding schemes are not precluded. UV sensors and door sensors may be associated with any emitter network under the command of the central computer.

An integral part of the sterilization system is the data logging and reporting performed by central computer 11 as shown in FIG. 1A. Data logging provides various capabilities to this system, such as recording door open/close events, recording pause/resume events, recording configuration changes, and providing auditing based upon what user is using the system, what the user does, and how effectively rooms are disinfected. Further, electricity usage may be monitored in order to detect lamp or ballast failures.

Upon commencing a disinfection job, a data record is created indicating the location being treated and start time. This record may be kept in central computer 11, and a copy may be transmitted and posted on a secure web server with access only by authorized users with valid access information including a password. Once the first set of UV sensor readings are received by the computer, the estimated time to completion is calculated by the computer based upon the target UV dosage and the actual incident intensity measurements. An update may then be made to the job data record which may include the latest sensor readings, estimated time to completion, and elapsed time. Other data items including starts, stops, job termination, patient identification numbers, and pathogens being treated for may be tracked and reported as well. A unique benefit of this reporting system is the ability for sharing of real-time data among different departments of the facility using the system. In the case of a hospital, the admitting department will benefit from such reporting by having the ability to plan when to send patients to a room based upon the estimated job completion time. Or the cleaning department manager can use the real-time data to locate an employee and track their productivity. The infection prevention department may configure reports to aid in determining the efficacy of their disinfection protocol and to track problem patients or areas of their facility. There are other benefits to real-time access to job data and they are not precluded. An additional feature is the ability to post jobs to be performed to this system via a remote web server. This feature affords interested departments the ability to plan and schedule resources and to plan patient room assignments.

Figure 1:
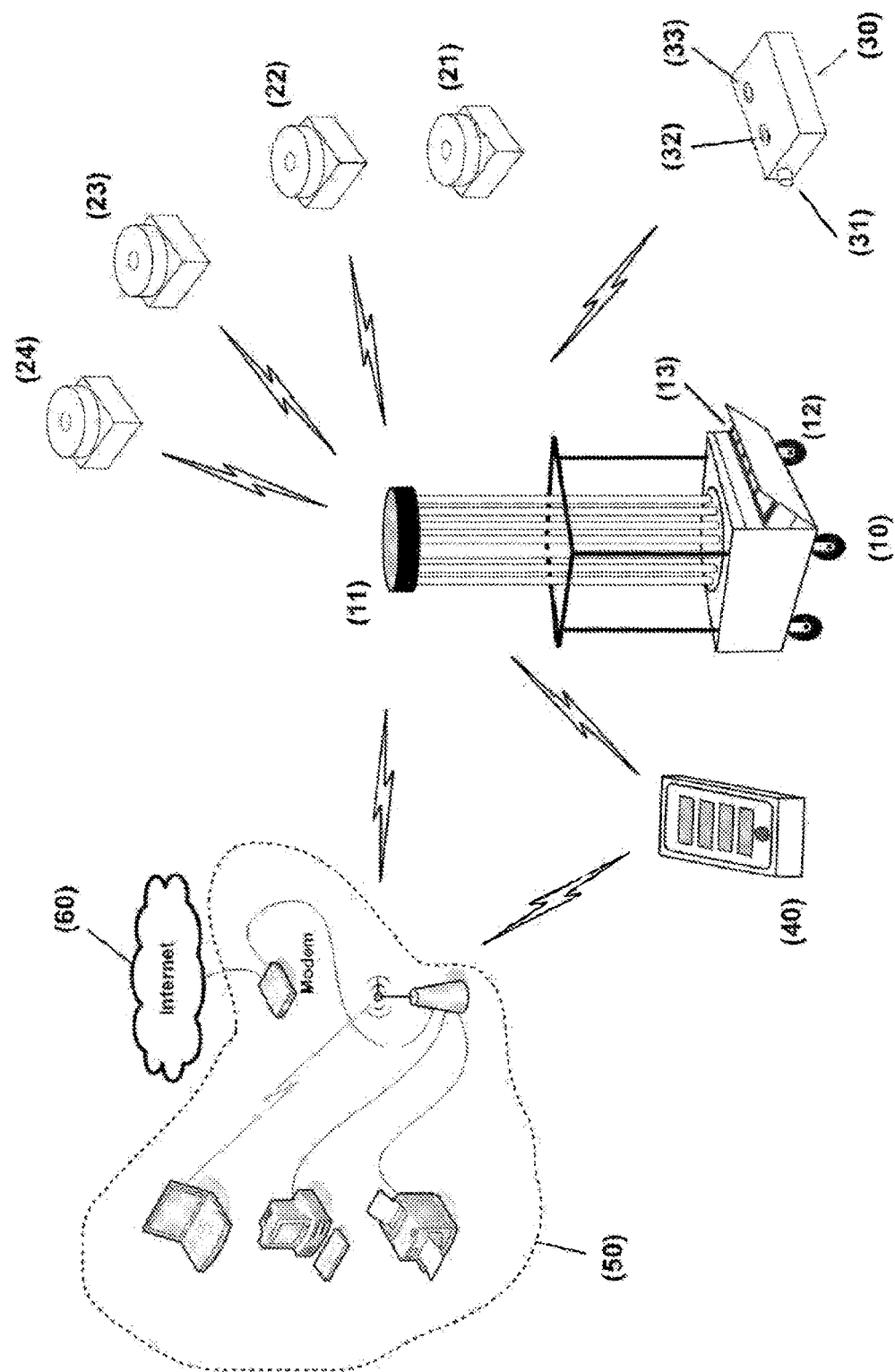
FIG. 1B is a perspective view of a disinfection system with the addition of a UV sensor storage compartment with charging capacity.

The system may employ an Internet Protocol address sharing scheme, which enables two or more wireless computing devices shown in FIG. 1, central computer 11 and remote control 40, the ability to communicate with each other inside of, or behind, a firewall. Typically, the devices acquire an IP address dynamically from the hosting DHCP server so none of the devices can predict the address of any other device. The devices are capable of communicating with the Internet through the firewall, but their local network addresses are translated as their messages are sent out to the Internet. The firewall may not accept incoming traffic except in response to an outbound message.

There is no local name-server in which the devices can store their names and network addresses. The problem becomes a question of how the devices find each other so they can communicate. Within the present disclosure, this may be solved by having central computer 11 capture and send its local untranslated IP address to a remote Internet host. As the message is sent, the address of central computer 11 is translated (encapsulated) by the firewall, but the message payload contains the local untranslated IP address given by the DHCP server inside the firewall. Remote control 40, or another device, contacts the remote Internet host and reads the local untranslated IP address of the computer 11. Remote control 40, or other device, can now directly contact central computer 11 using the local untranslated IP address on the local network inside the firewall. Although the Internet host is outside the firewall and cannot use the untranslated address directly, it can store the address that is scoped to the inside-the-firewall devices. Other inside-the-firewall devices can use the Internet host as name-server for local addresses.

In addition to allowing these devices the ability to communicate with each other, the host facility's firewall automatically blocks all attempts to communicate with them from devices located outside the firewall. All addresses are automatically updated to the remote Internet host any time a new IP address is obtained.

The central computer of the present disclosure may include its own web server, which may be accessed remotely. This allows an authenticated remote user to access local data and even remotely control the system.

In some embodiments, the devices may communicate with the Internet via a wireless telephone network (e.g. a cellular network). This may be advantageous in situations where it is not desirable to rely on the Internet connectivity of the facility.

The Internet connection, in whatever form, is also useful for such purposes as job reporting, remote system configuration, data backup, diagnostics, and remote operation.

FIG. 1B (in contrast to FIG. 1A) illustrates an emitting device with the inclusion of sensor holder 13, as well as emitter 10, a sensor holder 13, a sensing system consisting of UV sensors 21-24, door sensor 30, remote control 40, optional wireless local area network (WLAN) 50, and optional Internet connection 60 for the optional WLAN.

Figure 2:
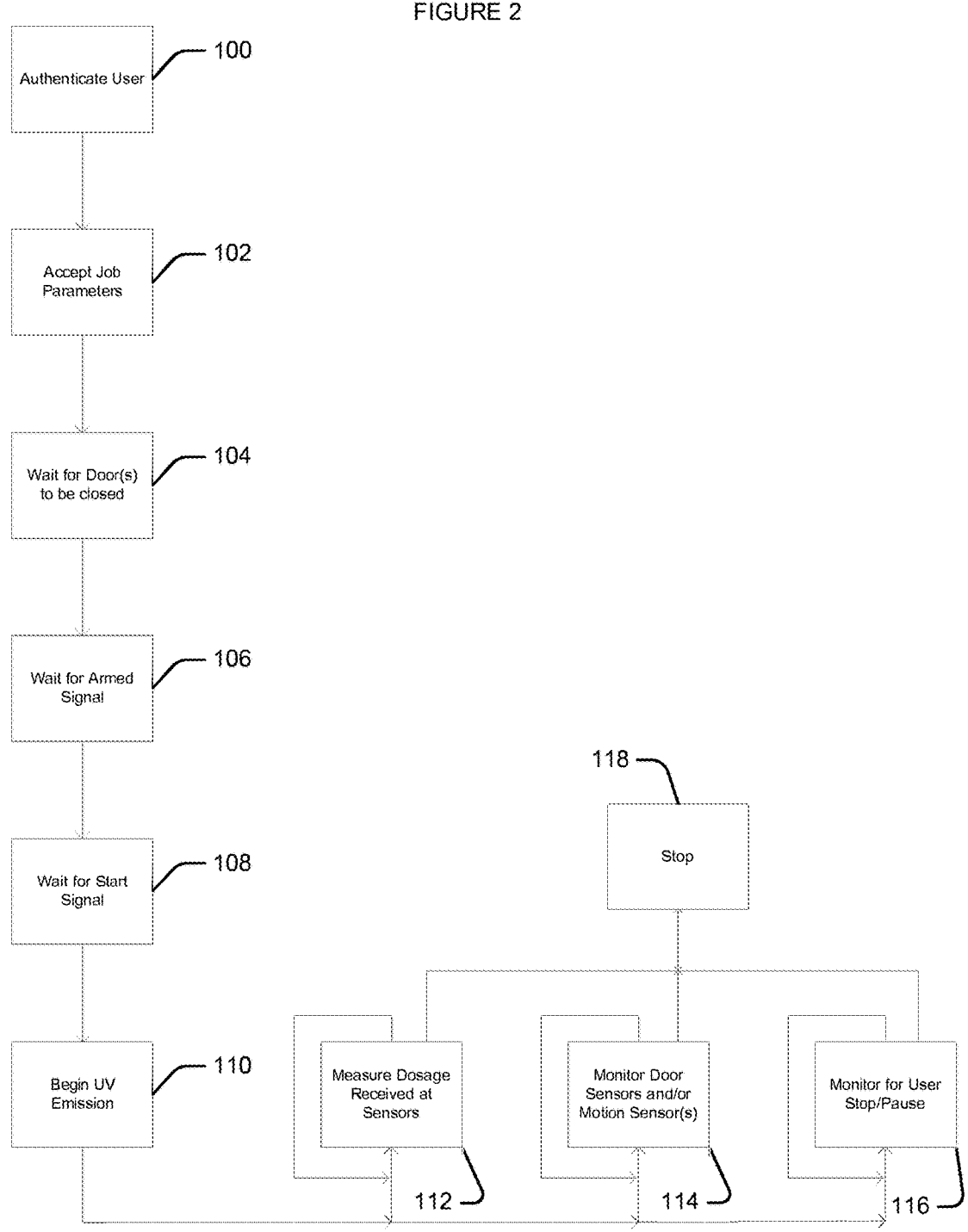
FIG. 2 is a process flow of a method of using the system of the present disclosure.

FIG. 2 presents a flowchart of one embodiment of how a device according to the present disclosure may be operated. At step 100, the user is authenticated via username and password, or any other suitable authentication means, at the remote control (or via an on-site or off-site computer).

At step 102, the user selects various job parameters to configure the system. These parameters may include such items as a name or numerical designator for the room/area being disinfected, a desired UV dosage based on the disinfection level desired and the pathogen(s) to be killed, and what set of peripherals to use in the cleaning. These peripherals include things like the door sensor(s) and UV sensor(s).

At steps 104, 106, and 108 the system waits for the door closed signal(s), armed signal, and start signal to occur, in order. Then at step 110, UV irradiation commences.

While the UV irradiation is in process, the system undergoes three loops: measuring the dosage received at the sensors 112, monitoring the door sensor 114 (which includes the emergency stop button on the door sensor) and/or the motion sensors, and monitoring for a user stop/pause instruction 116. When any of these monitoring loops detects its condition, UV irradiation is ceased. The three monitoring loops may advantageously occur at different frequencies. For example, the door monitoring loop is a safety concern, so it may be advantageous for it to occur at a higher frequency than the dosage monitoring loop. The user stop/pause monitoring loop may or may not be implemented as a listening loop; alternatively, it may simply be a command from the user that directly interrupts the UV irradiation. All of these embodiments are within the scope of the present disclosure.

FIGS. 3A through 5D show screenshots of some of the screens that may be displayed on the remote control of the present disclosure. In the embodiment shown, this software is running on Apple iOS. However, the remote control may provide the same or similar functionality through any of a variety of software platforms.

Figure 3A:
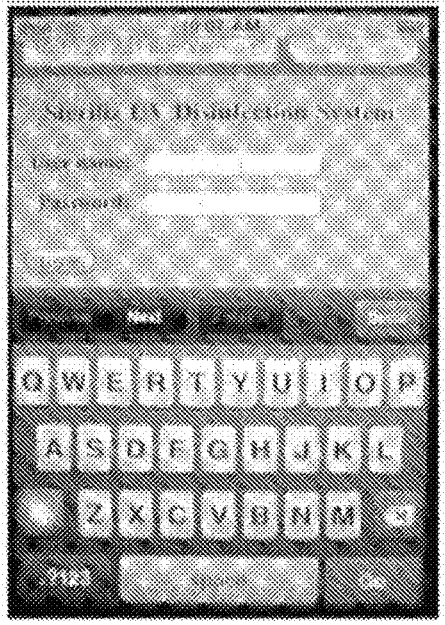
FIG. 3A is a screenshot from an exemplary remote operating device according to the present disclosure.
Figure 3B:
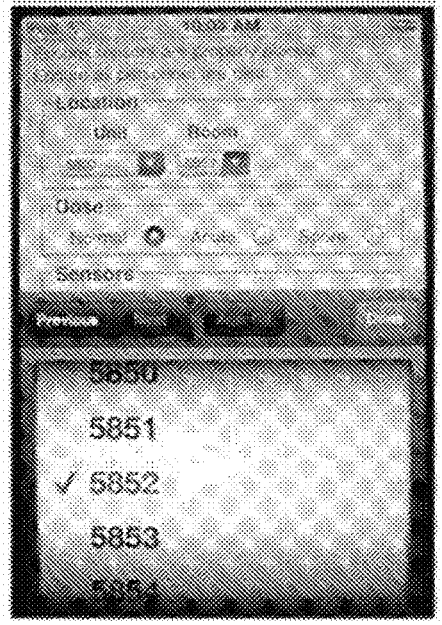
FIG. 3B is a screenshot from an exemplary remote operating device according to the present disclosure.

FIG. 3A shows a Login screen, allowing a user to authenticate via username and password. FIG. 3B shows a Disinfect screen allows the user to select the Unit, the room being cleaned, and the dosage desired. Rooms may be pre-programmed into the system for easy logging and auditing of cleaning procedures and then selected via drop down menus. One embodiment includes automatic position detection, via GPS, inertial positioning, Wi-Fi triangulation, or other suitable methods. The logging of treatment records allows 2D/3D visualizations of things such as untreated areas, areas with high treatment frequency, etc.

Figure 3C:
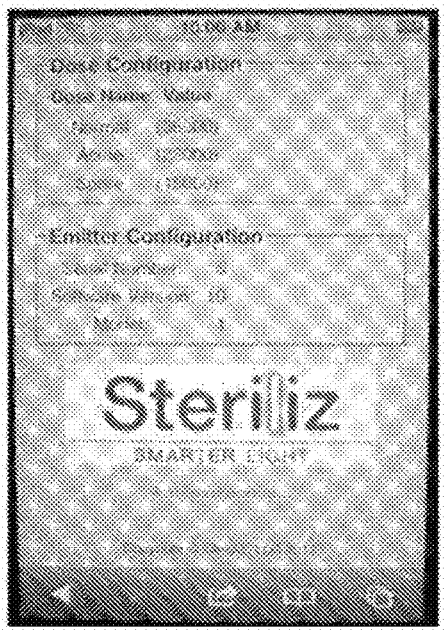
FIG. 3C is a screenshot from an exemplary remote operating device according to the present disclosure.
Figure 3D:
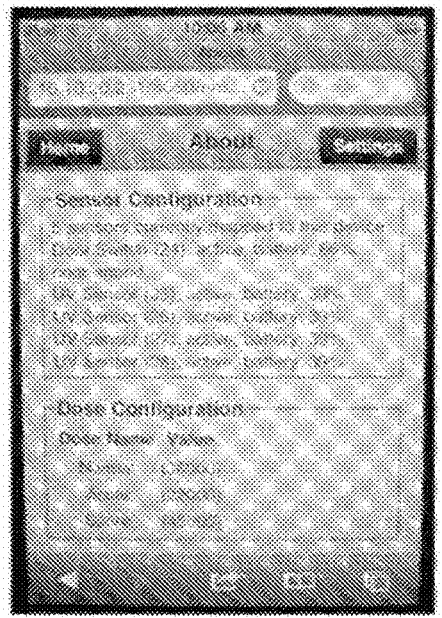
FIG. 3D is a screenshot from an exemplary remote operating device according to the present disclosure.

FIG. 3C shows the dose and emitter configuration. FIG. 3D shows an 'about screen', which lists the active sensors and their battery states.

Figure 4A:
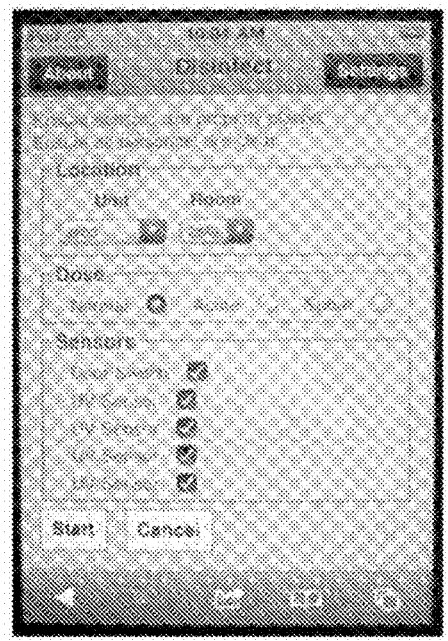
FIG. 4A is a screenshot from an exemplary remote operating device according to the present disclosure.

FIG. 4A shows the disinfect screen, ready to start. At least one UV sensor must be enabled in order for the system to operate.

Figure 4B:
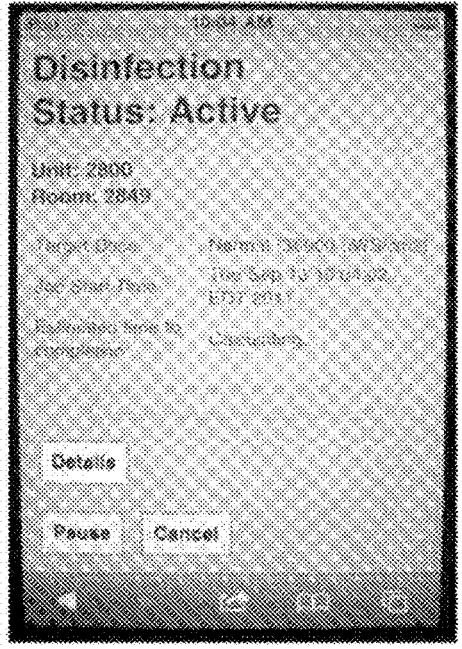
FIG. 4B is a screenshot from an exemplary remote operating device according to the present disclosure.

FIG. 4B shows a status page listing the parameters of the disinfection job and the estimated time to completion, which the system may calculate based on the UV light levels observed at the UV sensors.

Figure 4C:
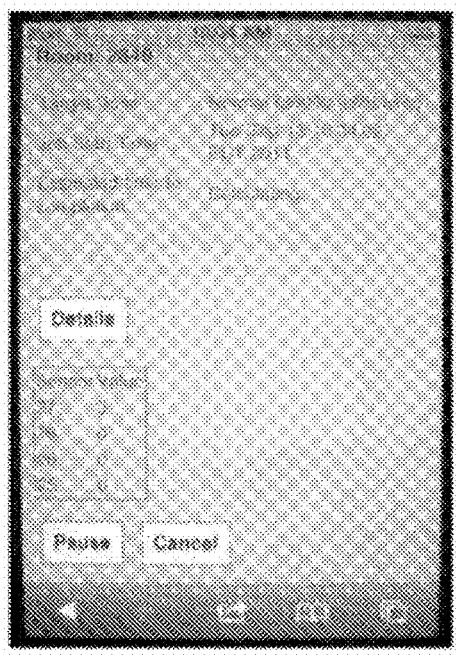
FIG. 4C is a screenshot from an exemplary remote operating device according to the present disclosure.

FIG. 4C shows the detail view available in FIG. 4B, demonstrating the levels observed at each sensor.

Figure 4D:
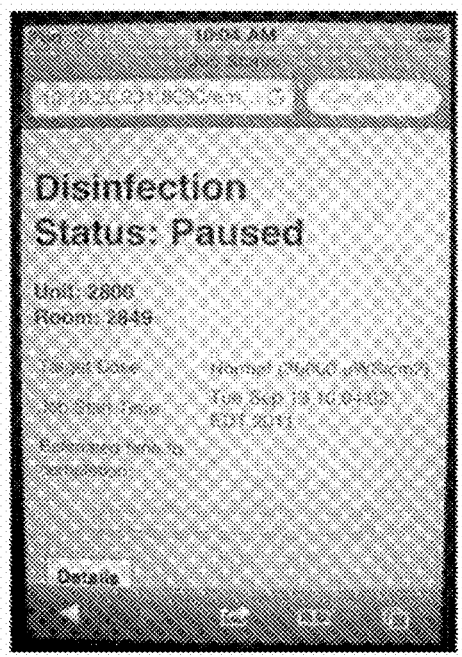
FIG. 4D is a screenshot from an exemplary remote operating device according to the present disclosure.
Figure 5A:
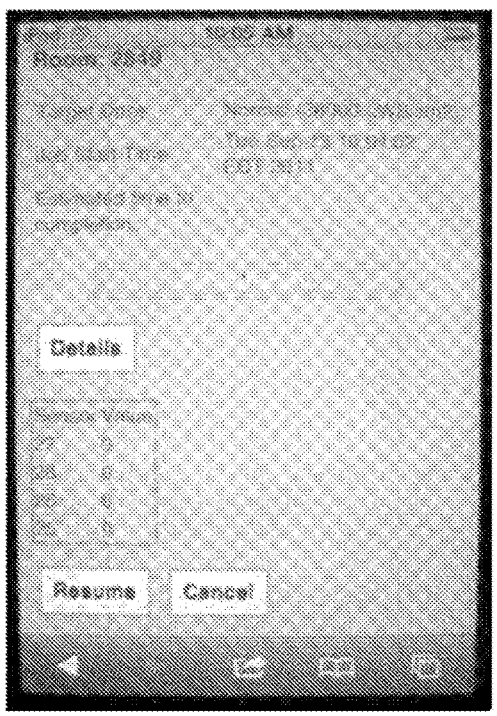
FIG. 5A is a screenshot from an exemplary remote operating device according to the present disclosure.
Figure 5B:
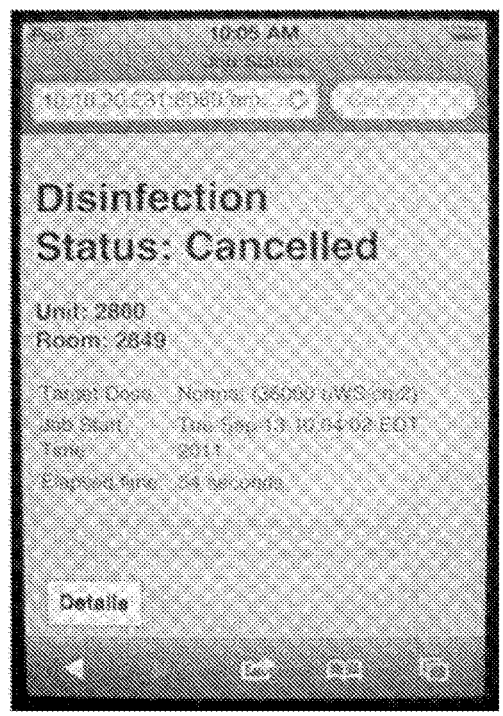
FIG. 5B is a screenshot from an exemplary remote operating device according to the present disclosure.

FIG. 4D shows the Status screen of a paused disinfection job, and FIG. 5A shows the option to resume or cancel the paused job. The job may be paused or canceled at any time by the operator via the remote control, so long as there is network connectivity between the remote control and the emitter. If connectivity is lost, the job may be stopped by pressing the emergency stop switch on the door safety sensor. FIG. 5B shows the Status page for a job that has been canceled.

Figure 6:
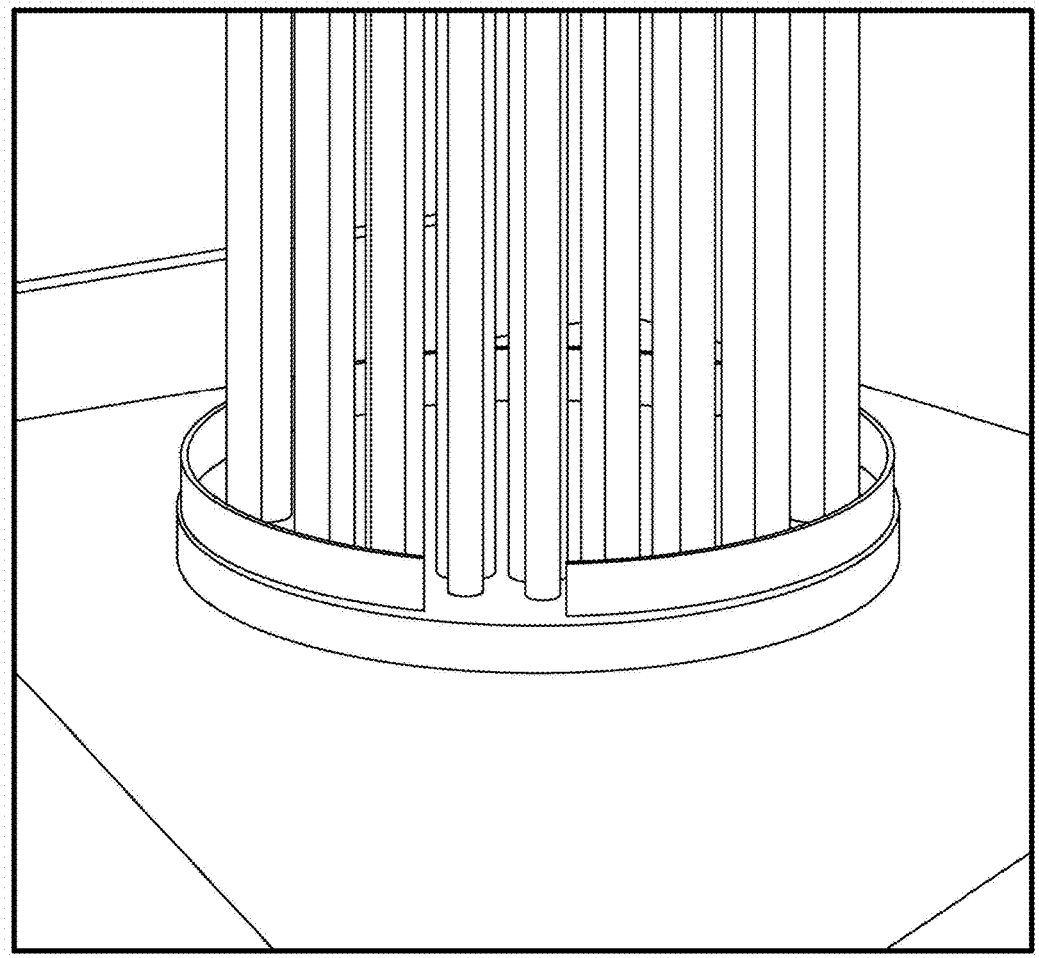
FIG. 6 illustrates an exemplary configuration of the emitting device.

FIG. 6 illustrates an exemplary configuration of the emitting device. This arrangement illustrates one method for the convenient replacement of the emission bulbs, wherein the cage can be rotated to a position corresponding with an opening for the removal and replacement of the bulbs.

Figure 7A:
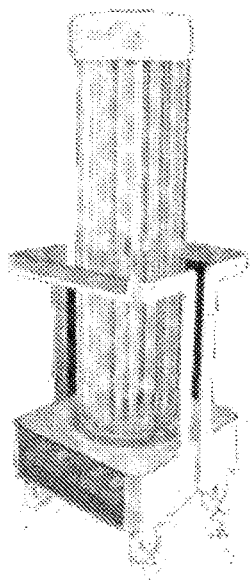
FIG. 7A illustrates an exemplary arrangement of an emitting device.
Figure 7B:
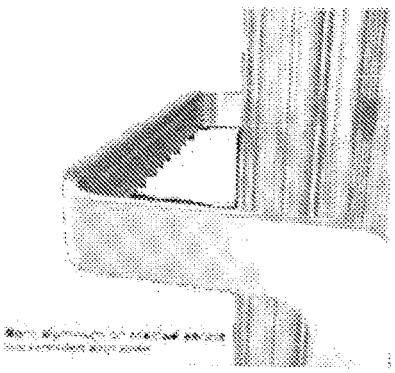
FIG. 7B illustrates an exemplary arrangement of an emitting device.
Figure 7C:
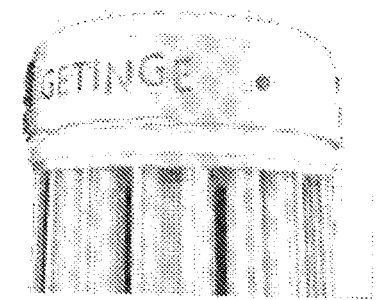
FIG. 7C illustrates an exemplary arrangement of an emitting device.
Figure 8:
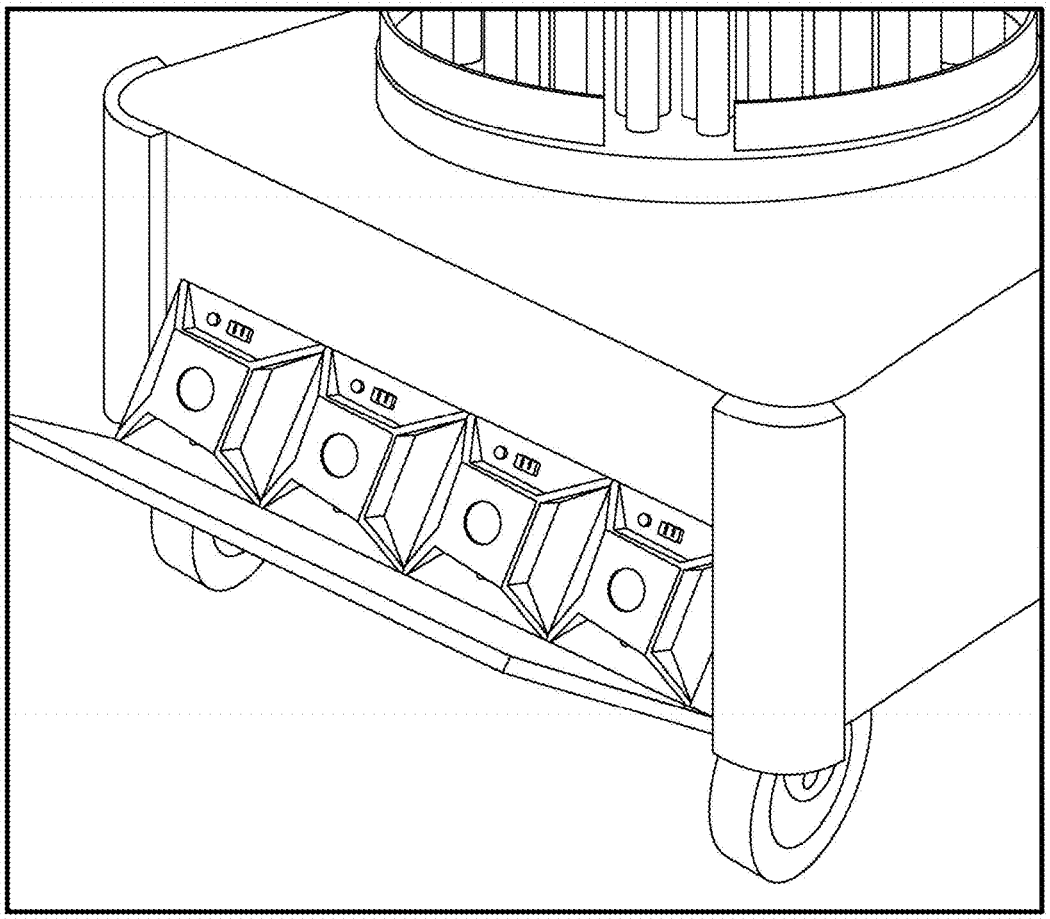
FIG. 8 illustrates an exemplary configuration of the charging connection between an emitting device and one or more sensors.

FIGS. 7A to 7C illustrate exemplary arrangements of an emitting device, including a configuration of the emitting device, the handles for the device, and a device with motion detection technologies.

Figure 9:
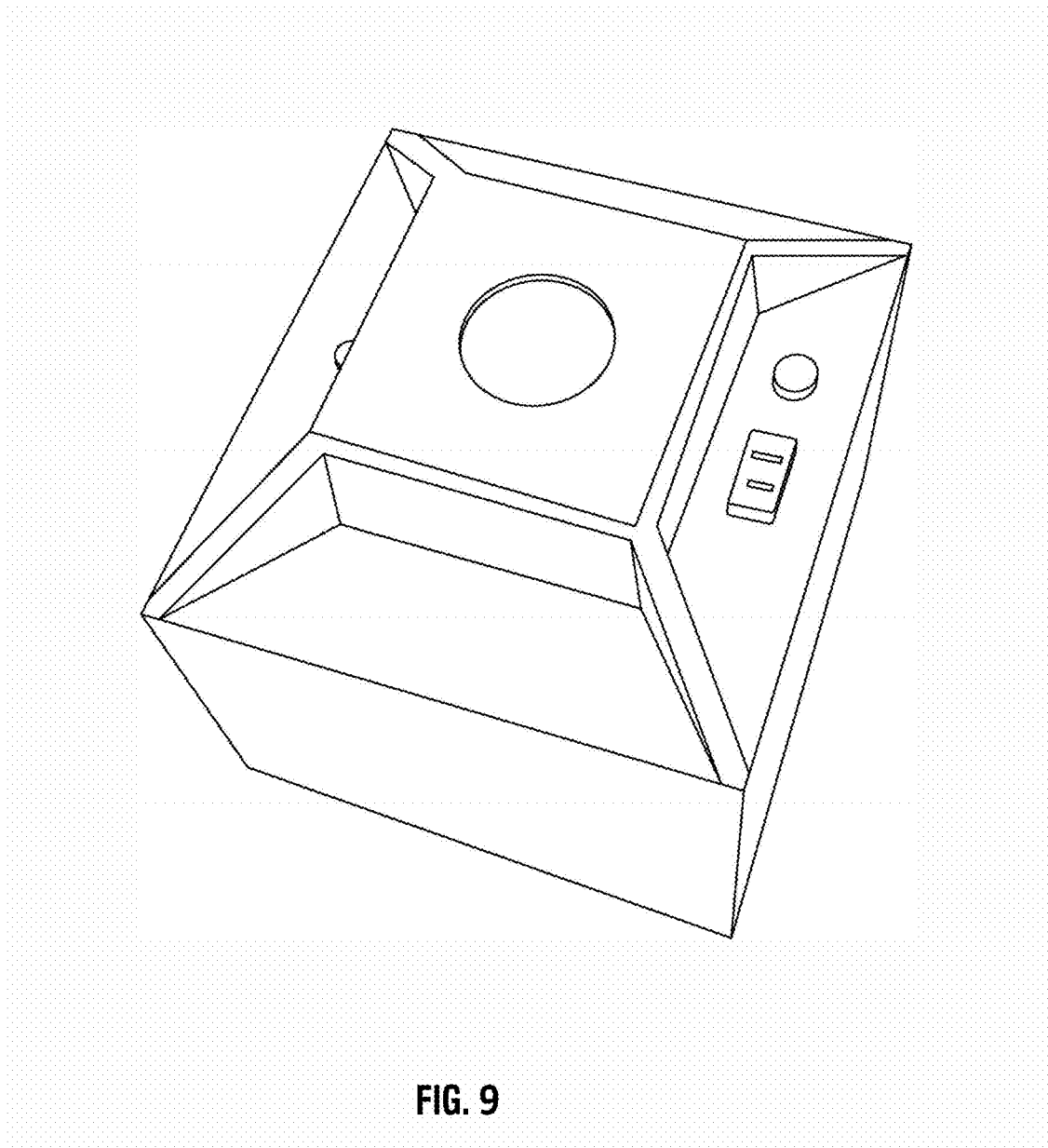
FIG. 9 presents an exemplary UV sensor as described in the present disclosure.

FIG. 9 presents an exemplary UV sensor with further details for an exemplary sensor provided in FIGS. 26A and 26B. As shown, a sensor may comprise a circuit for controlling, recording and transmitting. As well as one or more indicator lights, a UV sensor, and a battery.

In some embodiments, the UV sensors and/or the UV emitter device may also include a motion detector for observing the presence of any motion within the room being sterilized.

Figure 24:
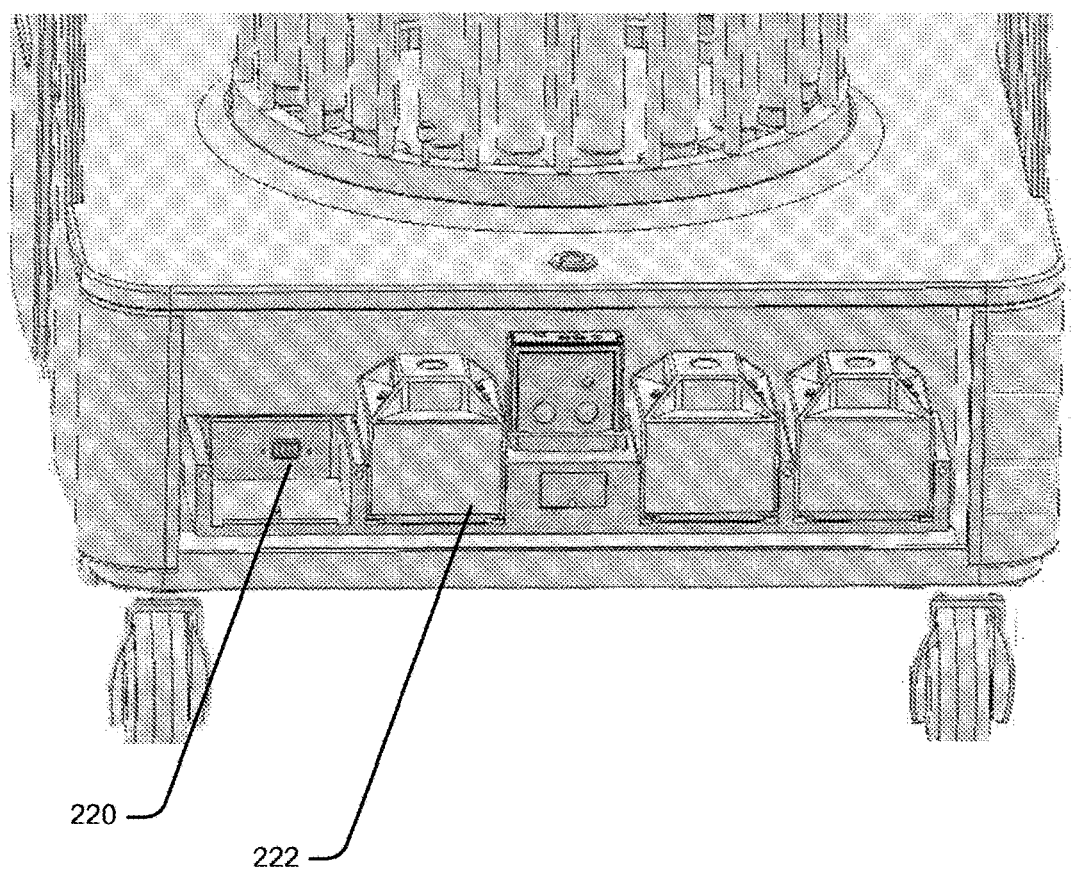
FIG. 24 presents in greater detail an exemplary connection for a sensor associated with an emitting device.
Figure 27:
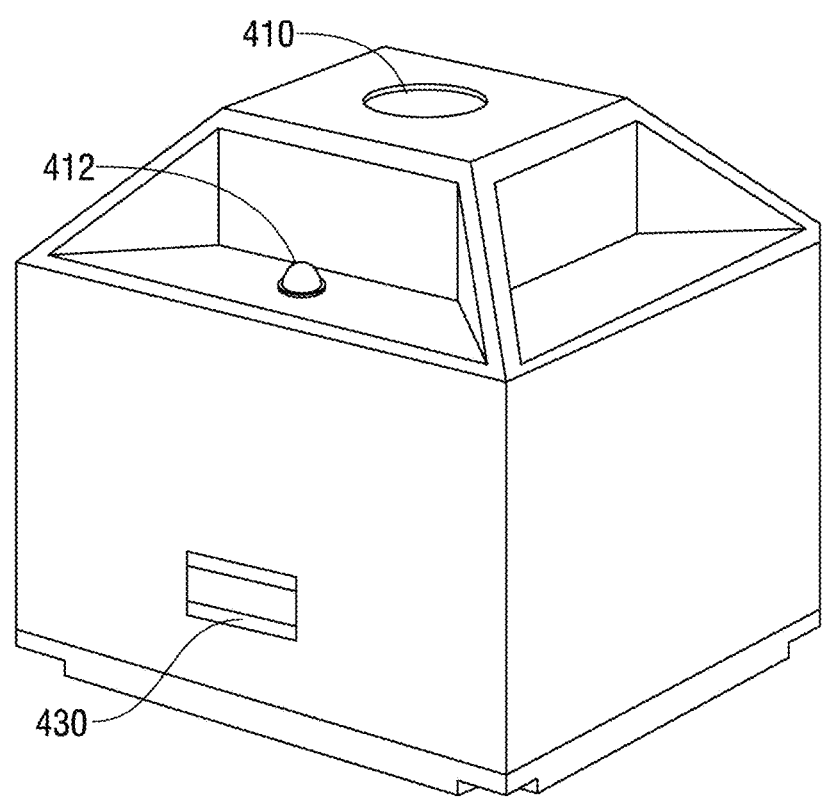
FIG. 27 presents in greater detail an exemplary sensor.

In some embodiments, a sensor may provide a charging connection to which a reciprocal charging connection may be provided on the emitting device. By way of example, FIG. 27 illustrates an arrangement for the charging connection on the sensor and FIG. 24 illustrates an arrangement for the reciprocal connection on the emitting or transportation device.

The present disclosure describes a system and method for the management and sterilization of a facility, such as in a hospital environment.

One embodiment comprises a software that is written in a computer programming language and may take or receive data from specific events that occur in a facility that have either been recorded previously or that occur in real time. Embodiments may provide detailed analysis of the data and may present it in a format that is easy to understand and interpret including text, color coded text, tables with text, tables with text and colors, graphs and charts both in color and/or monochromatic as well as other forms or data and analysis presentation.

Further embodiment may interface to other software or systems via any number of standard communications protocols including WiFi, Bluetooth, 3G, 4G, wired LAN, etc. Embodiments may also interface to hardware systems such as the R-D Rapid Disinfector manufactured by Steriliz, LLC, of Rochester, N.Y. The hardware systems include any system that records specific events that occur in a facility, which may include those that are related to infection control and management.

By way of example of one use of the present disclosure in a hospital environment, presented below are several departments a hospital that may interact with embodiments of disclosure for various different reasons.

Admitting:

An embodiment may monitor the list of rooms that need to be treated to manage patient room assignments through rearranging the order or priority in which rooms are treated;

A further embodiment may provide an estimated time of completion ("ETC") for estimating when a particular room will be complete and ready to occupy based upon historical treatment time of the rooms on the list and number of systems being operated at any given time;

A further embodiment may track, record and analyze when a room has been subject to a disinfection procedure to allow hospital admitting departments to send a patient to a completed room.

Environmental Services/Housekeeping:

One embodiment may monitor the list of rooms that require a disinfection procedure to enable staffing levels to be adjusted;

A further embodiment may track, record and analyze a particular operator's performance (treatment times, final doses, etc.) against historical data and statistics for the facility for training and review purposes;

A further embodiment may determine what operators have the most experience operating a particular device to identify the operator's parameters, for example which operators may be best suited to be trainers, etc.

Executive Management—C-Suite:

One embodiment may determine if a device is being utilized and at what percent of possible utilization the system is operating;

A further embodiment may compare the performance of a facility with known and/or other anonymous facilities as a means of comparison.

Infection Control:

One embodiment may schedule rooms than need disinfection procedures;

A further embodiment may confirm that an indicated disinfection procedure has actually been performed;

A further embodiment enables frequency reports to be generated for identifying problem areas within a facility;

A further embodiment may create a "to do" list of rooms when utilizing the system's "clean sweep" report.

Some of the aforementioned functions may take place automatically. For example, if the laboratory in a hospital determines a specific patient is infected with a "contact precaution" infection or disease (such as tuberculosis or MRSA, etc.) and the results of such a determination are entered into the hospital's own data management system then that system may be programmed so as to electronically send a notification to the system. In an alternative embodiment, the facility's database may be polled periodically for such data entries.

The above list is in no way complete and is intended to provide an exemplary use for the present disclosure, particularly in the context of a hospital environment. The use of the present disclosure in other environments where sterilization using UV radiation may be beneficial are not precluded.

Embodiments of the software component of the present disclosure may comprise several modules. Each module may provide a different report, graph, and/or chart which displays and provides the user with insight into the management of infection control within their facility.

Reports may have common user selectable settings which include: date range, location or group of locations (ie: unit or ward) treated, whether a job was completed or not, which machines were used, etc. Reports may be sorted by any of the preceding parameters.

Figure 11:
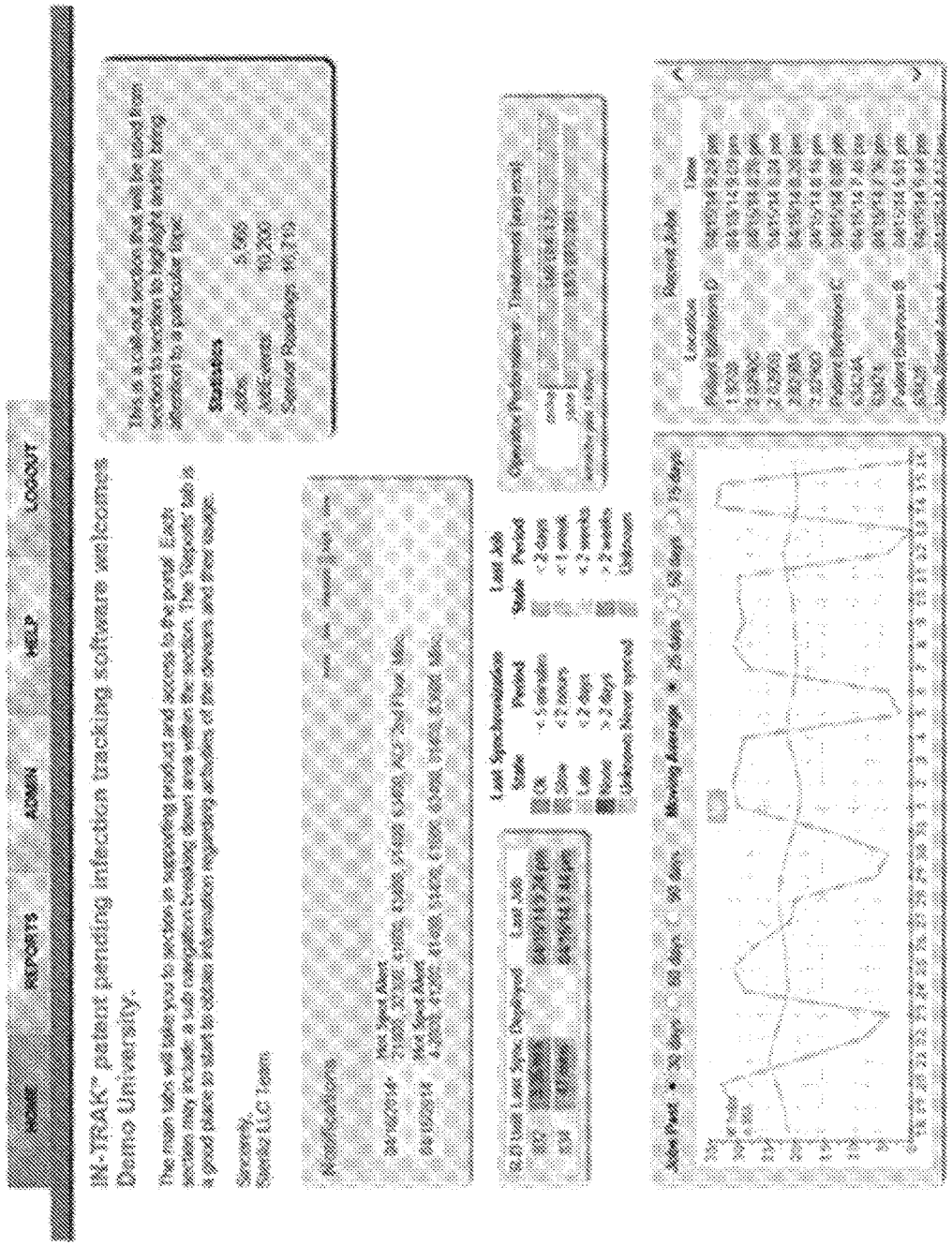
FIG. 11 presents an exemplary report as described in the present disclosure.

Reports may be scheduled to automatically run and be delivered to any of an unlimited number of previously determined recipients. By way of example FIG. 11 presents an exemplary report structure.

Reports may be viewed, printed or exported to other programs.

One embodiment of the system enables grouping of individual disinfection "jobs" into one "treatment" for reporting purposes. For example, in disinfecting a patient room the operator may only run one job by using a "pause, reposition, and resume" feature, which expedites the overall time necessary to disinfect. In alternative embodiments, an operator may perform more than one disinfection job in the room by running each separate job to completion.

In an example hospital environment, staff reviewing room disinfection reports typically want confirmation that an entire room was treated (or not), how long it took, who did it, when it was done, etc. They are not necessarily interested whether the operator performed one job or multiple jobs. An embodiment when used in this example, may combine all the separate "jobs" into one treatment based upon a moving time window concept. Other methods of combining the jobs into one treatment are possible and not precluded. For example the system may be set to use a four hour window in which case any jobs that were performed in a specific location within four hours of each other will be reported as one treatment. Individual job reporting is also available in the case where the analyst wants to see each separate job and not the combined treatment.

Figure 10:
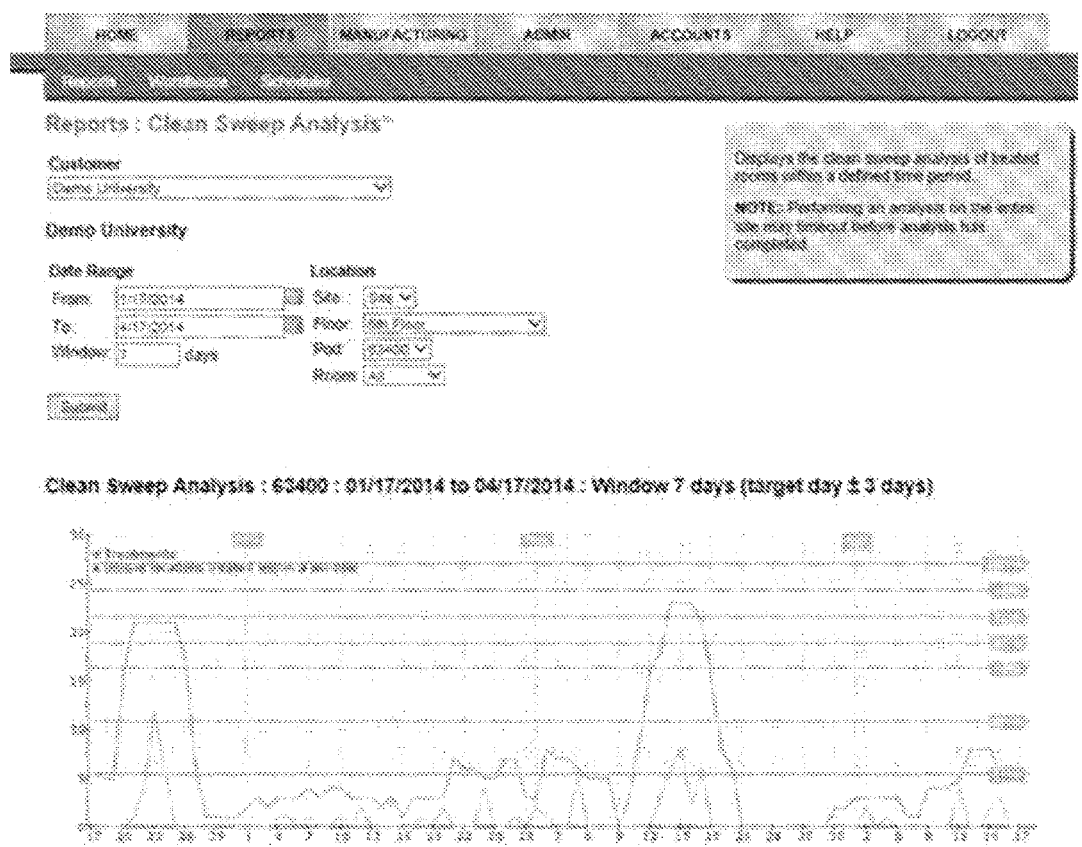
FIG. 10 presents an exemplary analysis report as described in the present disclosure.

By way of example, presented below are exemplary reporting modules that embodiments of the present disclosure may or may not employ:

FIG. 10 presents an exemplary analysis report as described in the present disclosure;

In the event a group of hospitals or a network of health care providers manage several facilities the aforementioned reports are available on a multi-facility basis thereby providing for significant data analysis and comparison capabilities.

Any and all of the foregoing reports, as well as others that are discussed herein, may be presented in 2 and 3 dimensional modeling for visualizing the reported results.

Room Disinfection Summary:

This may be simplified room disinfection report, which in one embodiment is presented as a text report that provides a listing of each room that was treated, the date and time it was treated, the operator who performed the treatment, the target dosage and or target amount of time to treat the room, and the final dosages for each of the sensors used in the room or time if sensors were not used, and the total elapsed time and active time for the system.

Figure 17:
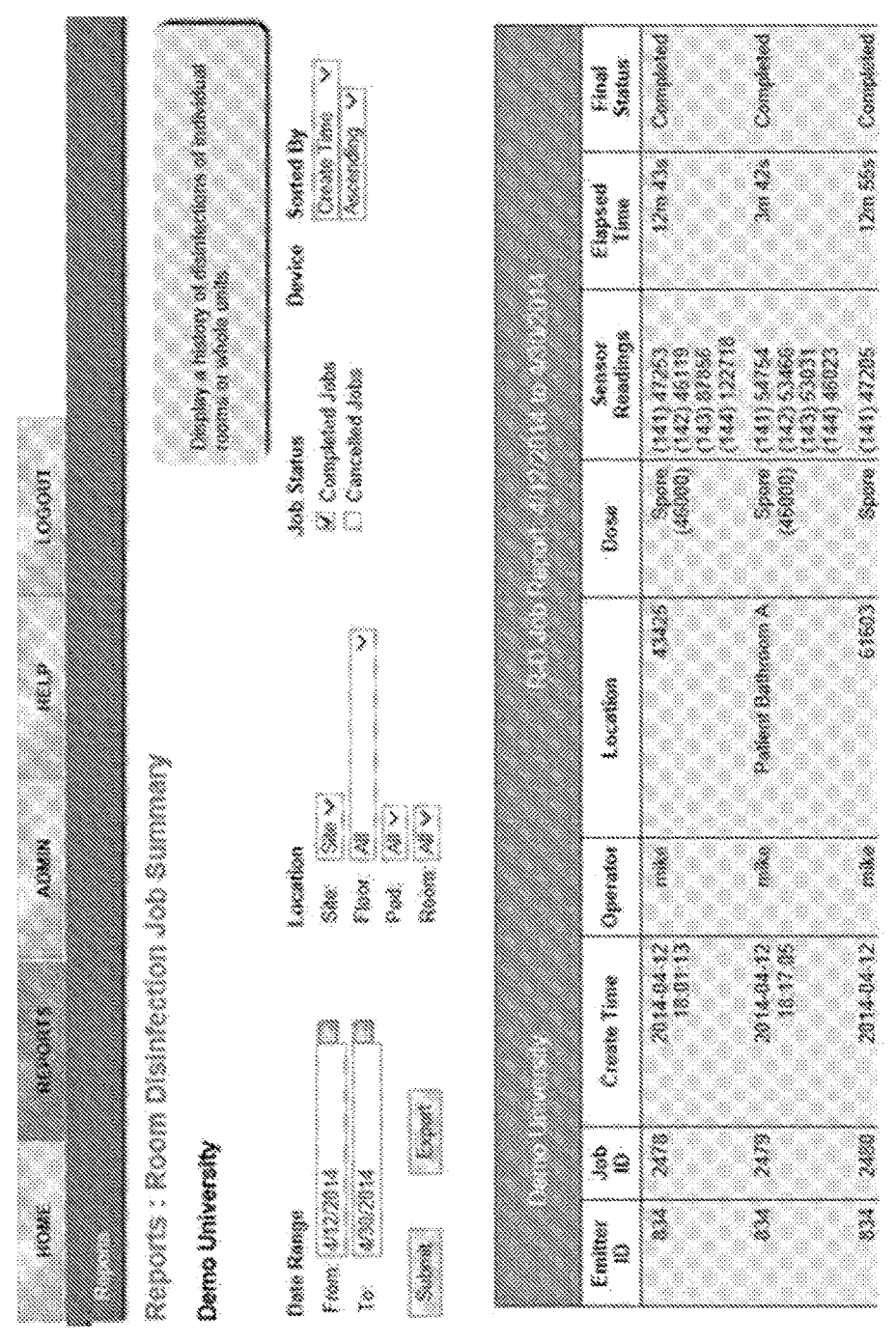

By way of example, FIG. 17 presents an exemplary room disinfection job summary report as described above.

Room Last Treated Report:

An example room last treated report may display details on the last treatment of an individual room within a time period. This is particularly useful, in the context of a hospital environment, if the analyst wants to know when a room or group of rooms were treated last.

Figure 20:
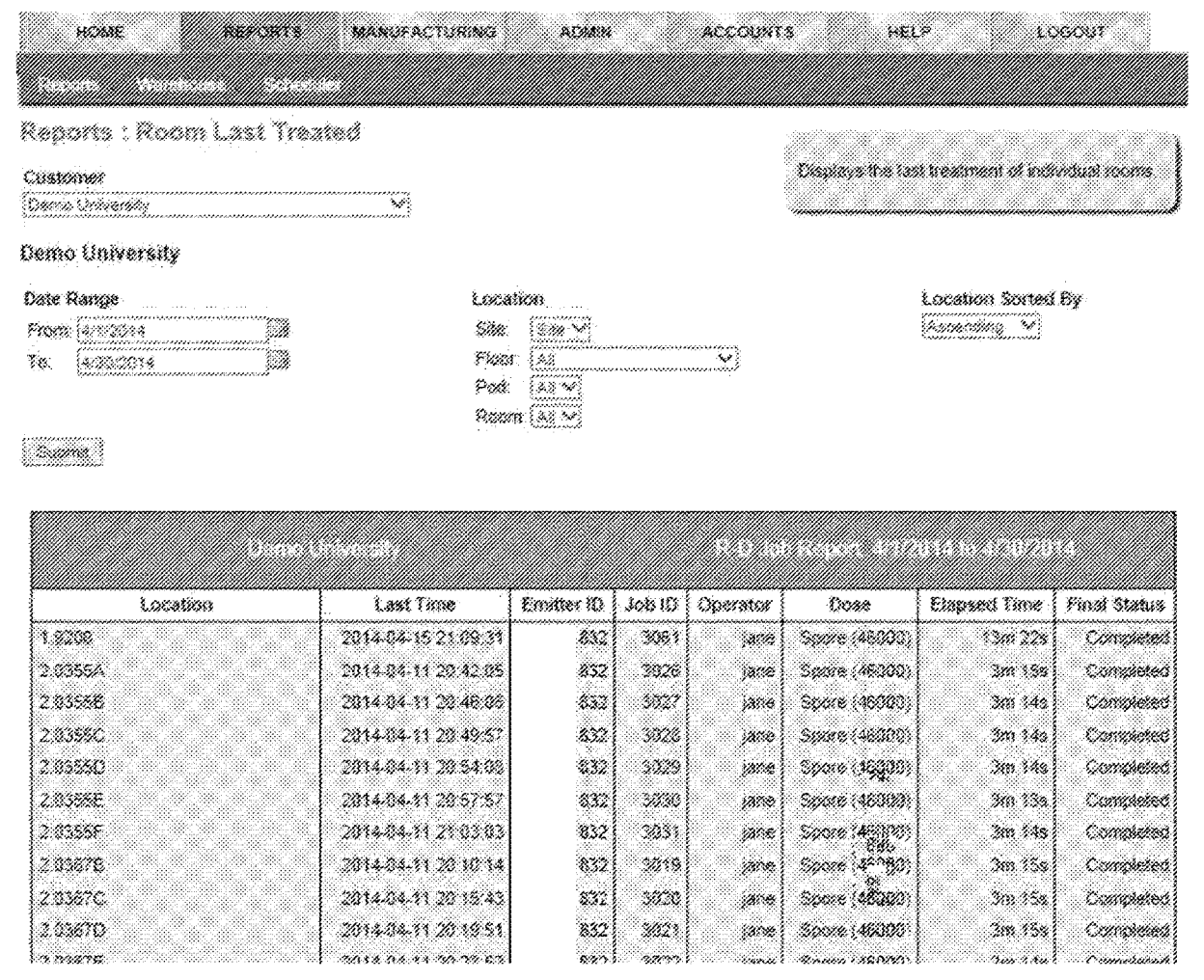

By way of example, FIG. 20 presents an exemplary room last treated report as described above.

Clean Sweep Report:

In the example case of a room being occupied by a person with a contact precaution disease or illness, a facility's policy may be for total cleaning of the entire unit or ward (i.e.: cleaning all rooms in the unit or ward)—a "clean sweep". Embodiments when used in this context, may generate a report that provides a list of rooms that are in a unit that have not been treated within a time period. For example, rooms 301-325 are in a ward and a person with a contact precaution is in room 312. The system responding to a discharge, may schedule, identify, and/or recommend the performance of a disinfection procedure for rooms 301-325 within a prescribed time period, i.e. 24-48 hour time period. In a further example, upon the onset of a "clean sweep", a report may show that all rooms have not been cleaned. As the cleaning progresses through the unit and more and more rooms are treated then subsequent reports may show fewer and fewer rooms that still need to be treated right up until the expiration of the time window.

Figure 16:
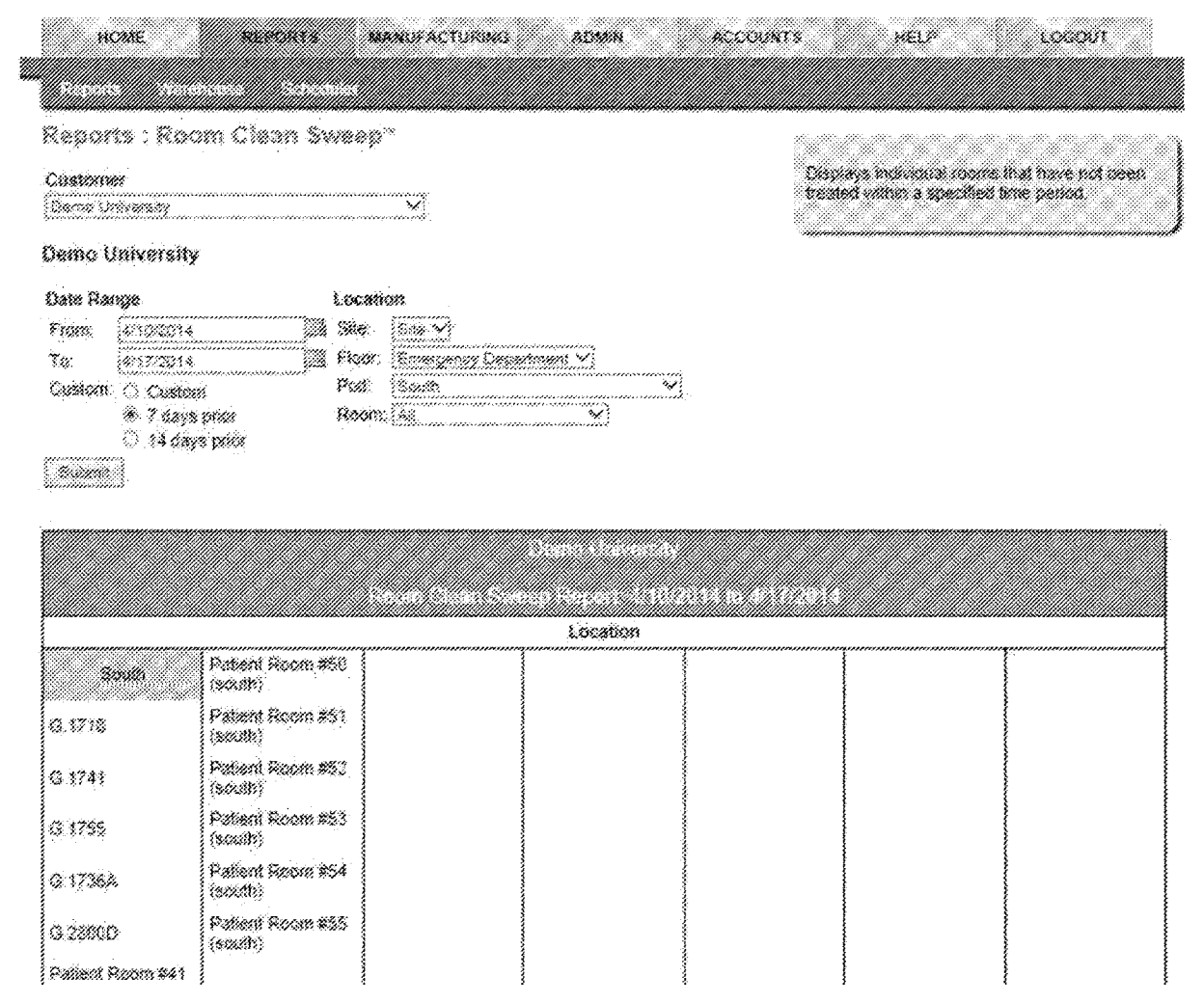

By way of example, FIG. 16 presents an exemplary room clean sweep analysis report as described above.

Room Treatment Frequency Report:

An exemplary room treatment frequency report may display data for the frequency, or number of times, a selected group of rooms or individual room has been treated in the specified time period. This may indicate there is a contamination problem with a particular room or group of rooms or units.

Figure 19:
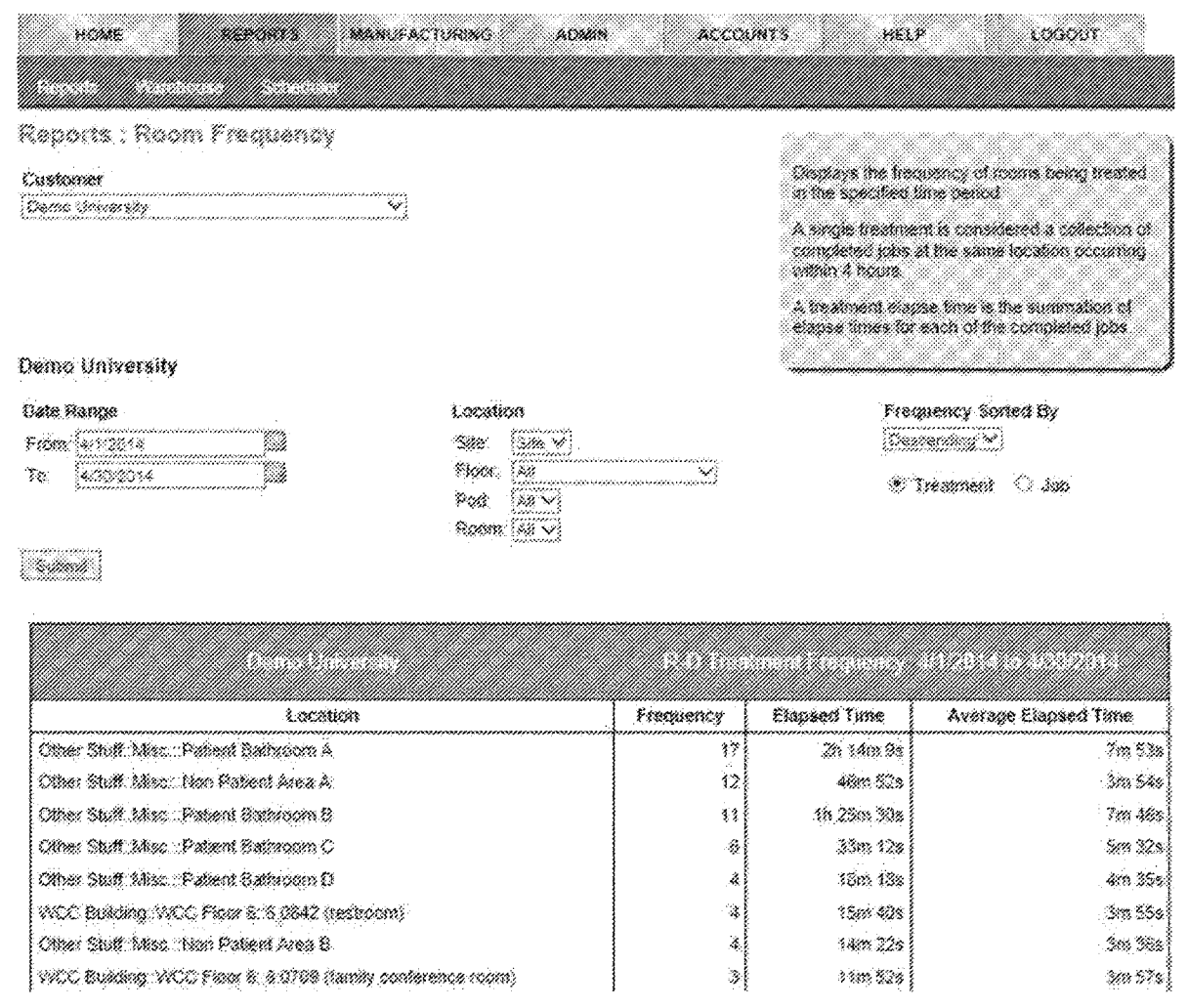

By way of example, FIG. 19 presents an exemplary room frequency report as described above.

Room Hot Spot Report:

An exemplary room hot spot report may combine data and colors into a single report table giving the analyst significantly more insight into the movement of infectious disease within a facility. The listing of a particular room, unit or entire facility can be shown with a color overlay for each room indicating the number of treatments that have occurred in each room based upon a predetermined legend. The number of treatments may also be displayed for each room as a text entry.

Figure 13:
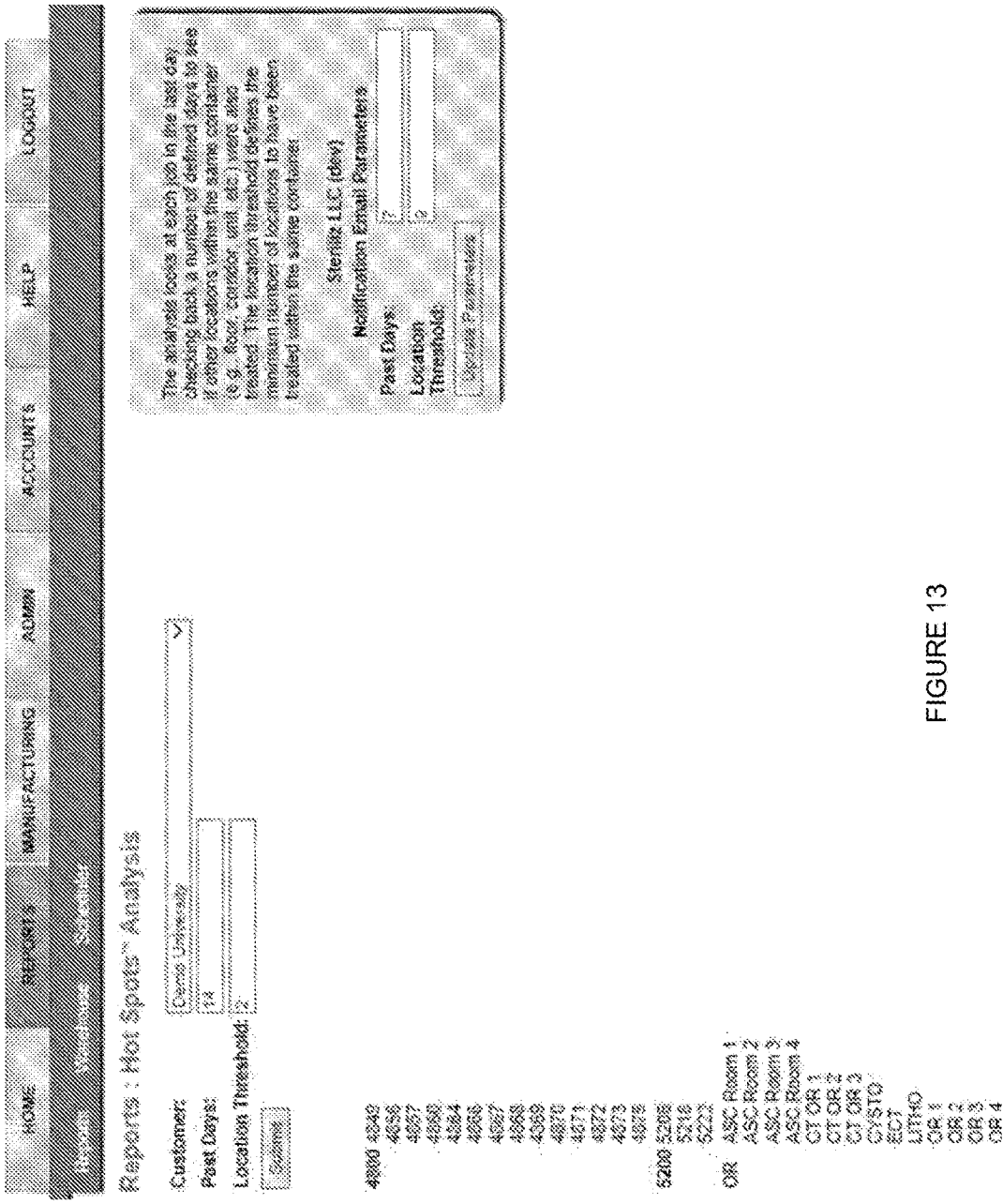
FIG. 13 presents an exemplary hot spot analysis report as described in the present disclosure.

By way of example, FIG. 13 presents an exemplary hot spot analysis report as described above.

Room Overview Report:

An exemplary room overview report may displays a color coded table of rooms that have and have not been treated within a time period thereby providing the analyst with a visual plan to "treat" all rooms within the facility within a specified time period.

Figure 21:
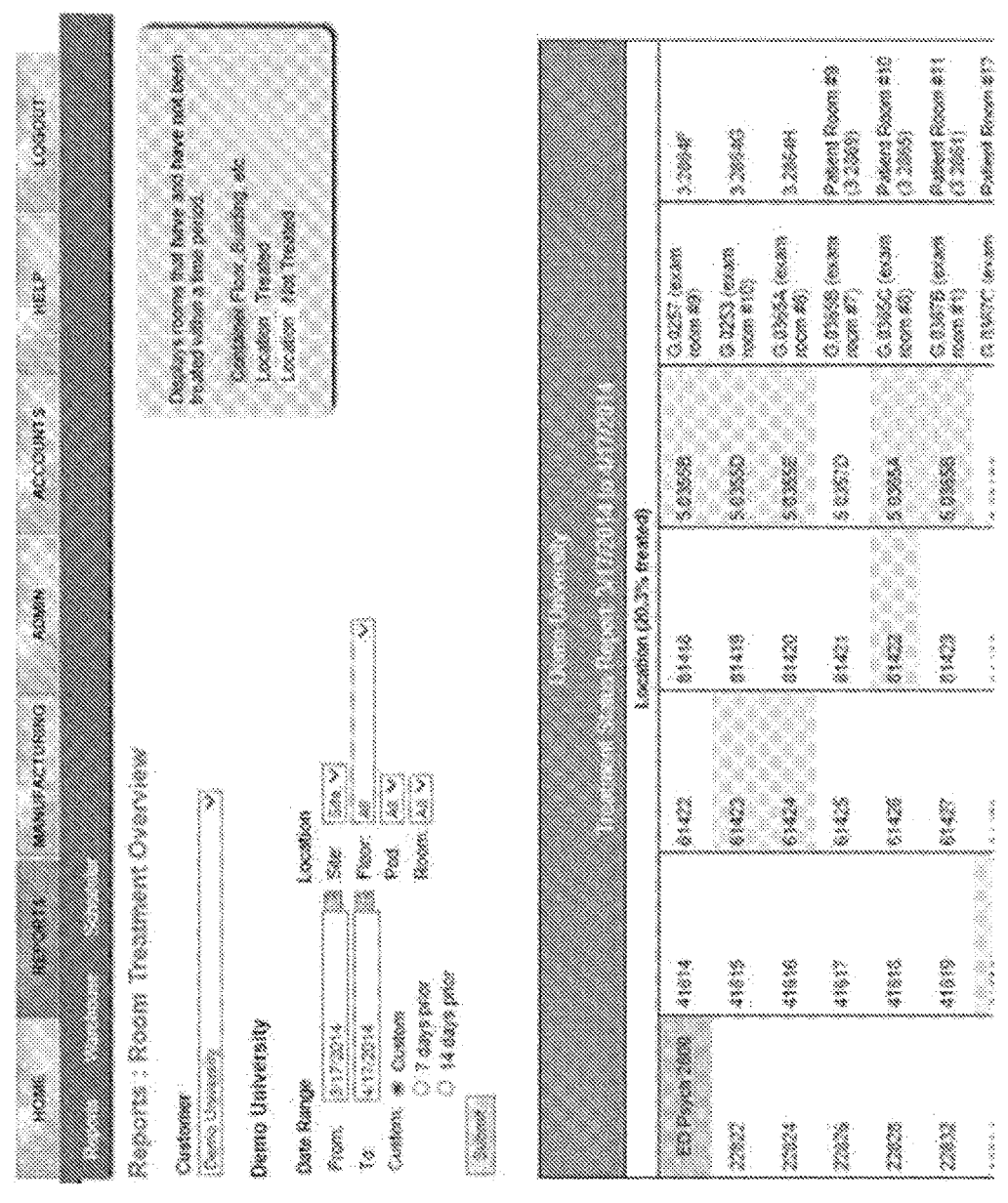

By way of example, FIG. 21 presents an exemplary room treatment overview report as described above.

Room Statistics Report:

An exemplary room statistics report may be presented in a table form to display locations being (or to be) treated, treatment count, total elapsed time for all treatments, and average elapsed time for treatment in the indicated room. Embodiments may enable facility management to access key statistical treatment time data to compare operators' performance and allow for better management of staff and equipment.

Figure 22:
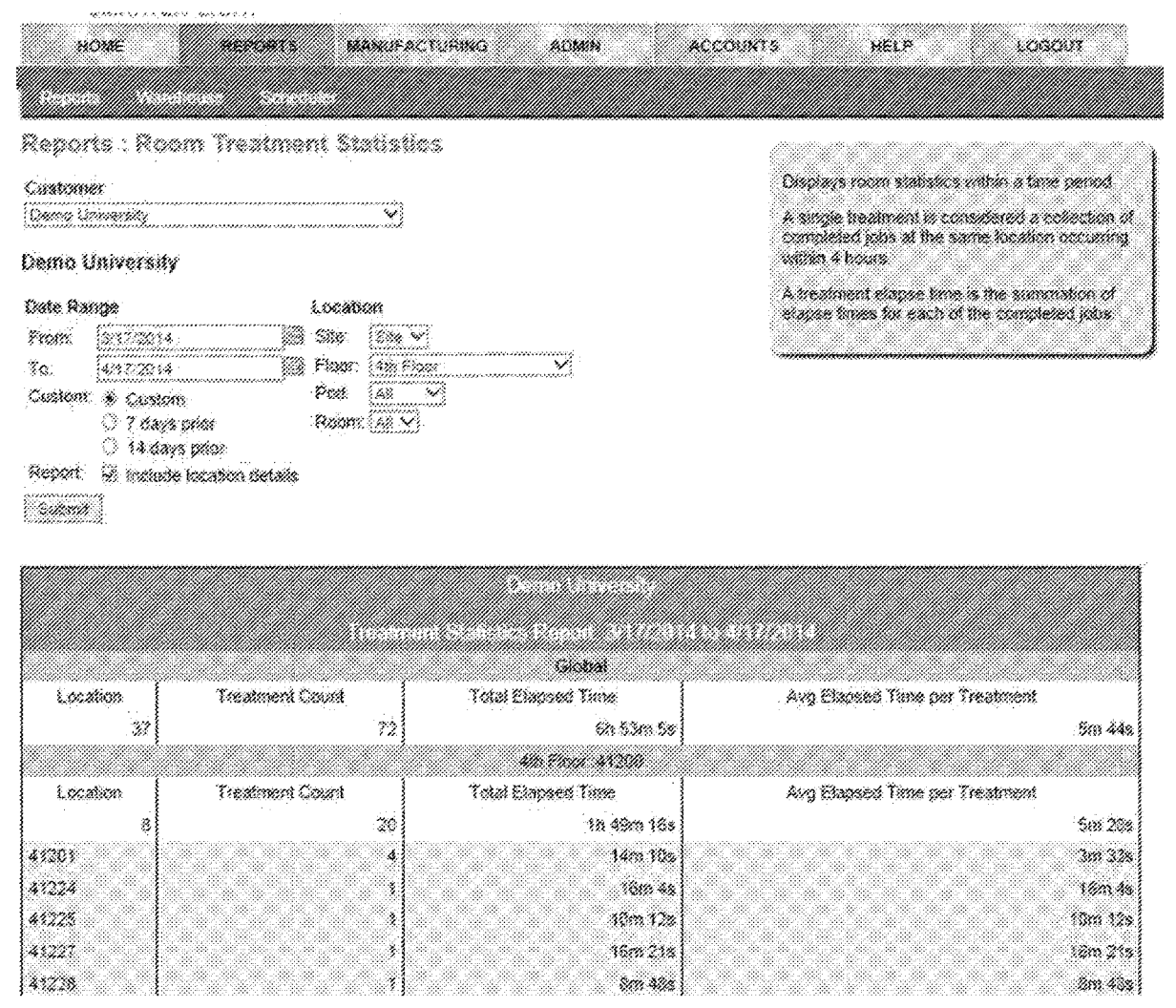

By way of example, FIG. 22 presents an exemplary room treatment statistics report as described above.

Team Performance Report:

An exemplary team performance report may be in the form of a bar chart for displaying the number of treatments performed by each of the respective operators within a given analyst determined time period, and the average amount of time for each treatment. This output may then be used to verify that the operator has complied with performance standards, i.e. minimum UV exposure time of a room.

Figure 23:
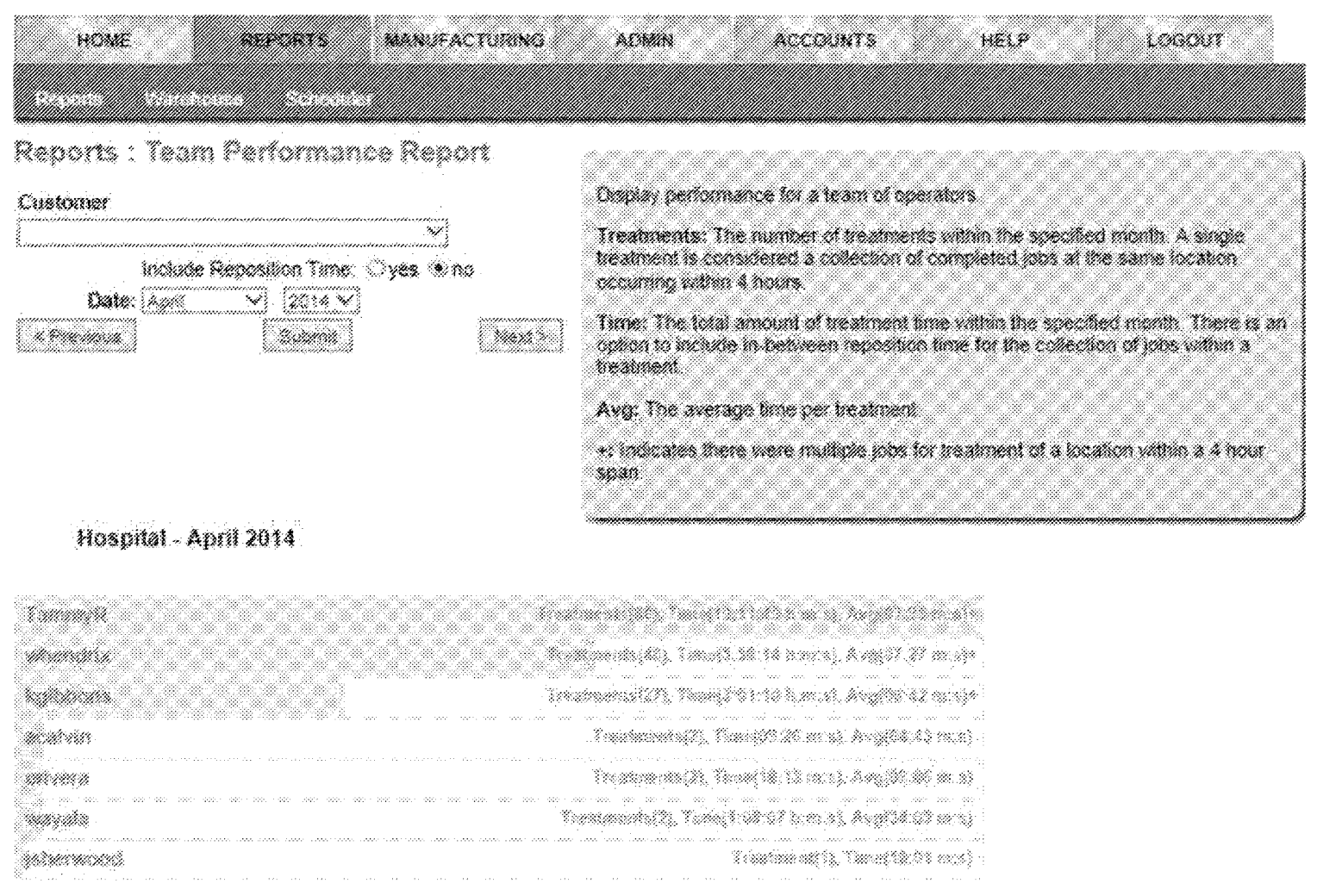

By way of example, FIG. 23 presents an exemplary team performance report as described above.

Device Utilization Report:

An exemplary device utilization report may be presented as a bar chart report to provide facility management with utilization information on a day by day, week by week, month by month, or year by year basis. This enables facility management to compare infection rates intra- and inter-hospital. Furthermore, this exemplary report enables an analyst to correlate usage of the system against infection rates.

Figure 12:
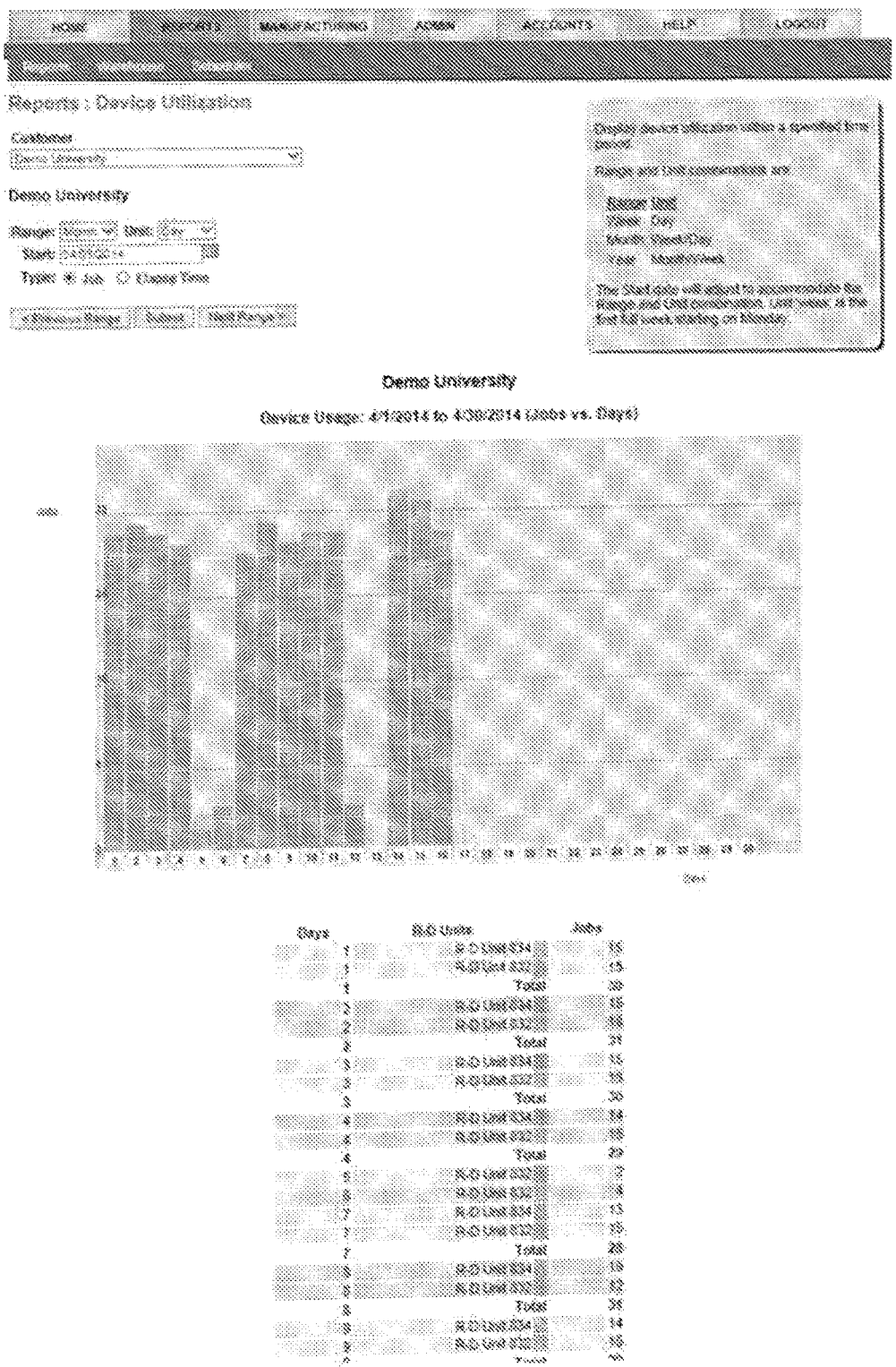
FIG. 12 presents an exemplary device utilization report as described in the present disclosure.

By way of example, FIG. 12 presents an exemplary device utilization report as described above.

Room Listing Report:

Examples of this report present in a simple, easy to interpret format data associated with all the programmed rooms within a facility.

Figure 14:
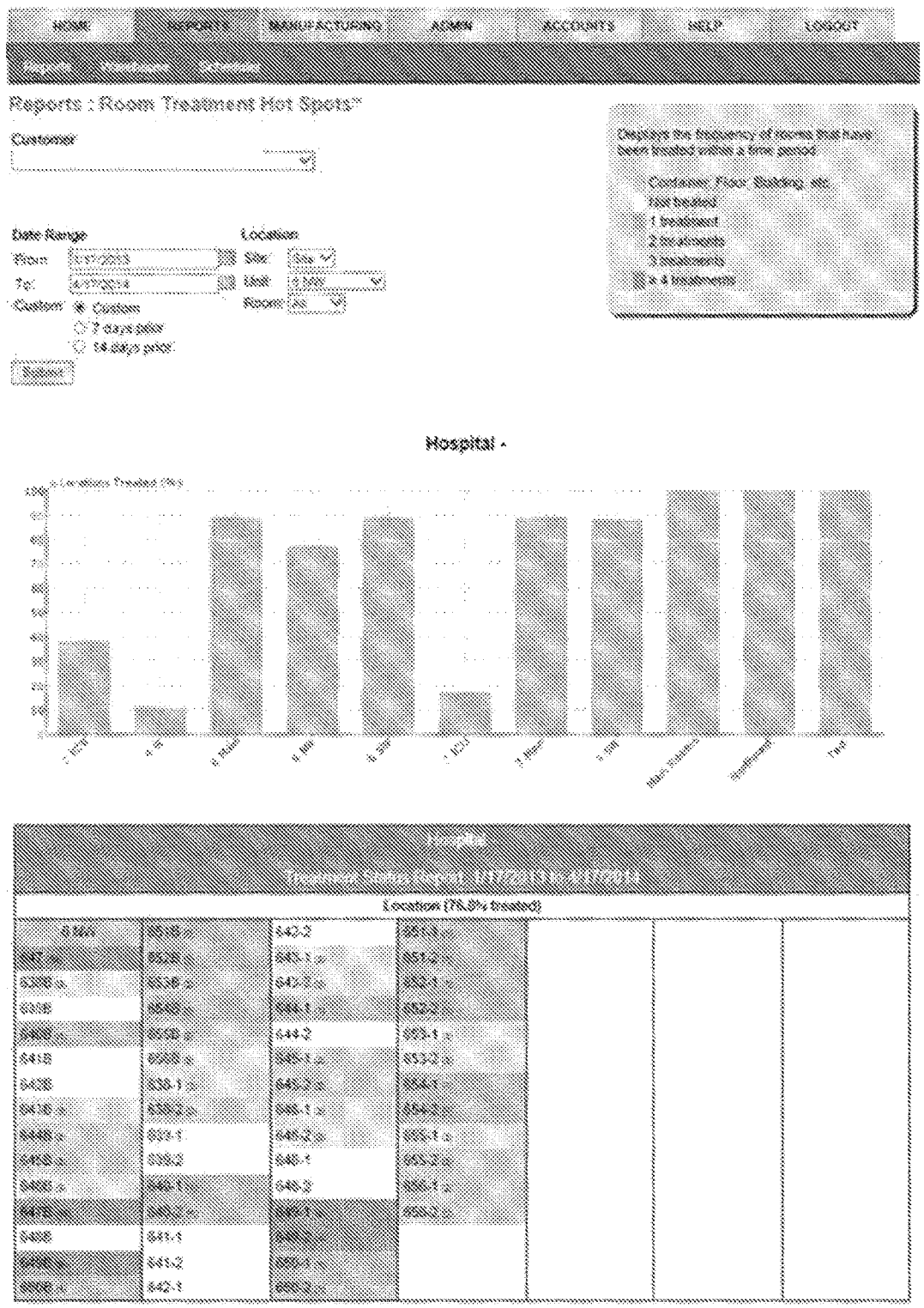
FIG. 14 presents an exemplary room treatment analysis report as described in the present disclosure.

By way of example, FIG. 14 presents an exemplary room treatment analysis report.

Figure 18:
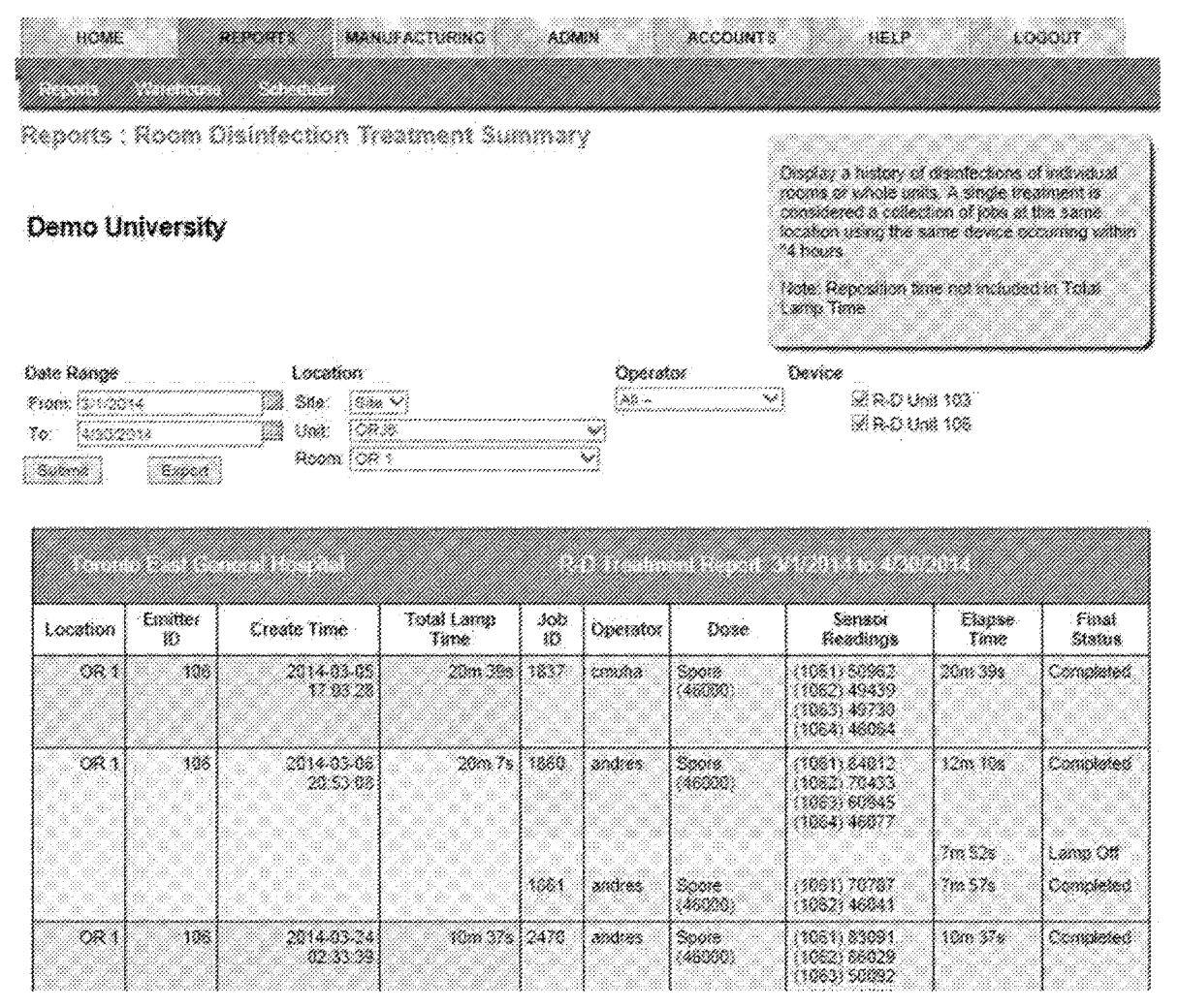

By way of example, FIG. 18 presents an exemplary room disinfection treatment summary report as described in the present disclosure;

A further embodiment of the present disclosure provides a means for automatic or manual repositioning of the emitter, or emitters if multiple emitters are used to improve the disinfection efficacy and performance, which can be caused by way of example by: shadowed areas not receiving a sufficient dosage of UV light necessary to eradicate targeted pathogens, and long treatment time due to distance from the emitter to the pathogen. An embodiment may employs a drive wheel that enables the emitter to be repositioned to a new location in the space being treated.

This embodiment may be controlled by the computer and may be operated based upon sensor measurement feedback information, room layout including contents, completely random, or some combination of the various methods. Other methods of automatic repositioning are possible and are not precluded. Repositioning may also be done on a continuous basis so the emitter "crawls" throughout the space. An example application of this type might be to disinfect the hallways in a museum or day care center. Manual repositioning is also possible by the operator by disabling automatic mode. During repositioning mode, sensors that have received the desired dosage at their present location may be relocated to a new position and begin accumulating UV light from zero dosage. The computer may be manually told by the operator that a sensor has been repositioned or the use of motion detectors on the sensors or other location change schemes may be employed to automatically indicate the sensor location has been changed.

In a further embodiment, the sensors (21-24, 30), either wired or wireless, are provided with a convenient and easy method of storage and transportation to and from the environments to be disinfected. In one embodiment, the device provides a sensor holder integrated into the emitter, or emitter transport, which provides a convenient way to store, lock inside the emitter, and transport the sensors. An alternative to this design would be to have a holder that is separate from the emitter. Such a separate holder could be attached to the emitter on a temporary basis to transport the sensors, and may also have a way to lock the sensors inside or to the holder to prevent or deter theft. Other designs are possible and not precluded.

A further embodiment provides a means for the charging of the wireless sensors. This embodiment may include an on-board energy source, such as a battery, which will require periodic recharging. The recharging may take place either by connection to a battery charger or by using on-board solar panels, or a combination of both. Other methods of recharging are not precluded.

For example, the sensor holder may have electrical contacts that mate with electrical contacts on the sensors to accomplish the recharging. Induction charging is also possible thereby eliminating the need for such contacts. Further, energy harvesting may be employed to extend battery life before recharging by external means is necessary or to eliminate the need for a battery altogether. Some types of energy harvesting include photocells and piezo motion transducers however other sources of energy harvesting techniques are not precluded.

The present disclosure incorporates many other features to ensure safe and reliable operation. Some of them are as follows.

A password-protected remote control, which will only operate the system after a valid user name and password has been entered, prevents unauthorized use of the device.

A fail-safe lamp operating time limit also prevents damage to the lamps and overexposure of the room being treated. The present disclosure includes a built in timer limiting the "on time" for a treatment cycle. This may come initially programmed to limit the maximum lamp "on time" to approximately one hour. It may be changed to any amount of time up to, for example, two hours by an authorized service technician. In the unlikely event of a computer failure, the built in timer will turn off the lamps after the lamps have been on for the programmed amount of time, even if the job hasn't completed.

The present disclosure may also incorporate an internal circuit breaker that will turn off all power to the system in the unlikely event of an overload that is not protected by the facility's circuit protection system. In some embodiments, this may be a 20 amp time delay circuit breaker. This circuit breaker must be manually reset by a qualified technician. To protect against fires and thermal damage, the system may include an internal temperature sensor that will turn off all power in the event the internal temperature of the lower electronics cabinet is at or above the designed temperature limit.

This disclosure may also be equipped with a battery conservation system that automatically turns off power to on-board battery operated devices (including chargers for remote sensors, cooling fan and computer) when it has not been plugged into facility electrical power for a period of time. It is recommended that the device be plugged into facility electrical power when not in use.

The UV emitter may be equipped with two wheels that have push down brakes which, when depressed and locked into place, prevent them from rotating and spinning. The other two wheels are free to rotate and spin. They may be locked such that they can only spin and not rotate, like the rear wheels on a shopping cart.

A further embodiment includes the use of motion sensors to detect if people or animals have entered the space being treated as an additional safety feature. In one embodiment, the motion sensors may be located on the emitter unit and/or on the UV sensors. In a further embedment, the motion sensors may also be self-contained portable units that communicate either wired or wirelessly with the central computer. The motion sensors may employ one or more of several different technologies to detect motion of people and animals. One embodiment utilizes pulsed infrared (PIR) detectors. Other types of motion detectors include but are not limited to ultrasonic and laser technologies, and these and all other types of sensors are not precluded.

In a further embodiment, the normal operation the system employs both door sensors (as there may be multiple door sensors connected to a system) and motion sensors. In certain circumstances the operator may choose to use only one form of detector, either door sensors or motion sensors. One embodiment prevents operation of system in circumstances where a sensor is not being employed. A further embodiment may have exception for specially trained operators in situations where it is necessary to not use these safety sensors. For example in a museum where the operator manually pushes the system through the hallways and exhibit rooms wearing personal protection equipment, the use of the system without the use of sensors may require confirmation, or may be permitted on the basis of the operator wearing safety equipment for protection against UV exposure.

In a further embodiment, the computer for an active and emitting device, monitors the door sensors for a door opening condition which could mean a person or animal has entered the space being treated. If such a condition occurs the computer for the exemplary system pauses the job by turning off the UV lamps. The operator may then have the ability to reset the door sensors and resume the job without having to restart the job from the beginning thereby not losing any dose delivered up to the point when the fault condition occurred. The motion sensors, if employed, may produce a similar results—that is, during a job if motion is detected by the motion sensors then the computer may pause the job by turning off the UV lamps. The operator may then have the ability to resume the job without having to restart the job from the beginning thereby not losing any dose delivered up to the point when the fault condition occurred.

It should be noted that embodiments of the present disclosure may employ two different motion detection concepts, including position detection, and people/animal detection. Position detection may be used to determine if a UV sensor or the emitter has physically moved from a first to second position and also to determine the difference between the first and second position. Further embodiment may also employ people/animal motion detection to determine whether people or animals have entered the space being treated.

In a further embodiment, the system may automatically determine it's a location with a facility and furthermore, may report its location to a receiving system.

In yet a further embodiment, a system may learns its location adaptively over time. In yet a further embodiment, all rooms and locations are loaded into the facility database and when an emitter device visits a location for the first time the operator manually indicates where it is located. In further embodiments, system may know its absolute location and can then set that location to the operator selected room. The next time the system visits that same room/location it can determine its locations based upon the previous analysis.

In further embodiment, UV sensors may utilize relative or absolute location to determine, report, and record, the distance between emitter and the sensors. The facility may choose to require minimum sensor to emitter distances to help ensure the desired dose is delivered. The position data may also be utilized to determine when and where to reposition the emitter to minimize disinfection time and shadowed areas. The position may be manually changed by the operator or may involve automatic movement of the emitter via drive motors on the wheels to re-position the device automatically to minimize treatment time and shadowed areas. The position detectors may include accelerometers, triangulated wireless signals, GPS, inertial devices, or any other type of technology that provides position data.

There is the possibility that a UV sensor may be placed on a pathogen in a given location and then transported to another location and placed there. In this situation it is possible to unintentionally and unknowingly spread the pathogen to the second location. One embodiment of the system may employ antimicrobial material, for example a UV sensor may use antimicrobial material as the enclosure material. This may be accomplished by adding certain elements and compounds to the material during manufacturing. This feature may reduce or eliminate the transfer of pathogens. An alternative embodiment may utilize UV light to illuminate the sensors when they are placed into their storage base. This further reduces or eliminates any pathogen that may be on the sensors. There are other methods that may be employed to disinfect the sensors, in addition to UV, which include but are not limited to ozone, chemicals, and heat. These other methods are not precluded. Further embodiments may employ UV sensors with small feet located on the bottom of the sensors. These feet minimize the amount of surface contact between the sensor and the surface.

FIG. 24 illustrates one embodiment for a UV emitter, including charging connection 220, and one or more docked sensors 222.

Figure 25:
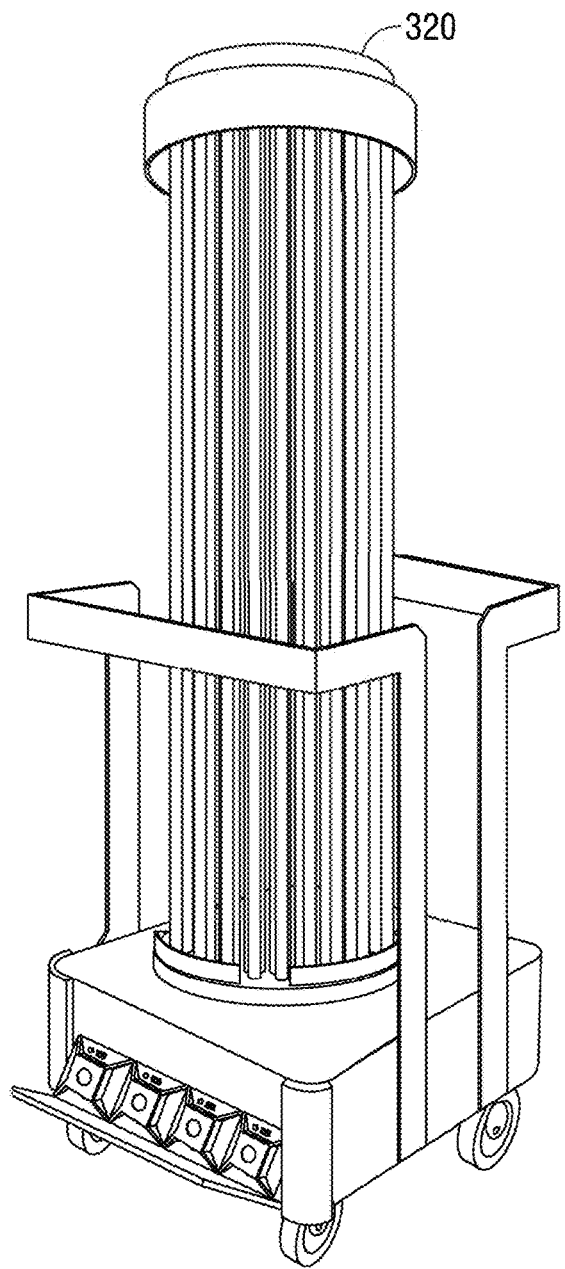
FIG. 25 presents an exemplary emitting device with motion detector(s).

FIG. 25 illustrates one embodiment of a UV emitter, including an exemplary location for one or more motion detector 320. Exemplary systems utilizing motion sensors on the emitting device, and/or the sensors, may be configured in a similar configuration as that of the door sensors. For example, the system could monitor communications from one or more motion sensor for a stop command associated with the detection of movement. In an alternative arrangement, the system may monitor for a no motion detected communication, or a combination thereof.

FIG. 26A illustrates the internal configuration for an exemplary UV sensor. As shown the exemplary sensor comprises: circuit 402, UV sensor 410, one or more indicator lights 412, and battery 414. FIG. 26B illustrates the configuration for a sensor enclosure 420.

FIG. 27 illustrate the external configuration for an exemplary UV sensor. As shown the exemplary sensor comprises: UV sensor 410, one or more indicator lights 412, and sensor charging connection 430.

A further embodiment of the UV emitter device may include a guard wires rod cage for providing physical protection to the bulb(s).

The foregoing description of illustrative embodiments is provided to enable a person skilled in the art to make and use the disclosed subject matter. Various modifications to these embodiments will be readily apparent to those skilled in the art, and the generic principles defined herein may be applied to other embodiments without the use of the innovative faculty.

What is claimed is:

1. An apparatus for disinfecting an area enclosure, and reporting said disinfecting across an area wide network; said apparatus comprising:
   a UV emitter for selectably emitting UV radiation for disinfecting an enclosure having an enclosure door;
   a computer operable to control emission of UV radiation by said UV emitter;
   a plurality of UV sensors in communication with said computer for measuring and reporting to said computer a dosage of UV radiation received, each of said plurality of UV sensors operable to measure UV light at a defined surface by placement of each of said plurality of UV sensors proximate to the defined surface; and further wherein at least one of said plurality of UV sensors is positioned remote from said UV emitter;
   wherein said computer is operable to pause UV emission at a first UV emitter position, and resume UV emission at a second UV emitter position;
   a door safety sensor in communication with said computer, said door safety sensor operable to detect and report whether the enclosure door is open or closed for maintaining integrity of the enclosure during emission of radiation by said UV emitter; and
   a human-machine interface (HMI) in communication with said computer operable to start and stop a disinfection procedure, and further operable to pause and resume said disinfection procedure; and
   a supporting structure for conveying said UV emitter;
      wherein said supporting structure comprises a means for receiving said UV sensors;
      wherein said supporting structure comprises at least two sensor receiver positions, wherein each of said at least sensor receivers comprises an electrical connection configured to electrically connect a received UV sensor to said supporting structure.

2. The apparatus of claim 1, wherein said door safety sensor further comprises an arming mechanism, said arming mechanism operable to prevent activation of said UV emitter unless said door is closed and said arming mechanism is active.

3. The apparatus of claim 1, wherein said door safety sensor and said plurality of UV sensors communicate with said computer using local area wireless communications.

4. The apparatus of claim 3, wherein said local area wireless communications comprises said computer polling said door safety sensor and said UV sensor.

5. The apparatus of claim 3, wherein said local area wireless communications comprises randomly timed transmissions from said sensors to said computer, said sensors being addressable to avoid collisions.

6. The apparatus of claim 3, wherein said local area wireless communications comprises a wireless access point, said wireless access point being integrated into said apparatus.

7. The apparatus of claim 1, wherein said computer communicates with said door safety sensor more frequently than with said plurality of UV sensors.

8. The apparatus of claim 1, wherein said UV sensor are battery-powered.

9. The apparatus of claim 8, wherein said UV emitter further comprises at least one charging connector for said battery-powered UV sensors.

10. The apparatus of claim 1, wherein said UV sensor comprise cosine-corrected UV sensors.

11. The apparatus of claim 1, wherein said human-machine interface communicates with said computer using local area wireless communications.

12. The apparatus of claim 1, wherein said human-machine interface communicates with said computer using wide-area wireless communications.

13. The apparatus of claim 1, further comprising at least one drone emitter unit, said at least one drone emitter unit providing additional UV light.

14. The apparatus of claim 1, further comprising a wireless network adapter to provide internet access.

15. The apparatus of claim 1, further comprising at least one device chosen from the group consisting of: a humidity generating device, an ozone generating device, and a vaporized hydrogen peroxide generating device.

16. The apparatus of claim 1, wherein said UV emitter comprises a plurality of substantially uncovered UV lamps.

17. The apparatus of claim 1 wherein at least one of said plurality of UV sensors are operable to detect a motion within said environment and communicate detection of said motion to said first computer.

18. The apparatus of claim 1, wherein
   said at least two sensor receiver positions are substantially recessed within said supporting structure.

19. The apparatus of claim 1, wherein at least one of said plurality of UV sensors is configured to reduce transfer of contaminates.

20. The fixed or mobile apparatus of claim 19, wherein at least one of said plurality of UV sensors comprises feet for elevating body of said at least one of said plurality of sensors thereby decreasing surface in contact with said surface for limiting transfer of contaminates.

\* \* \* \* \*